(12) United States Patent
Wu et al.

(10) Patent No.: US 6,872,716 B2
(45) Date of Patent: Mar. 29, 2005

(54) ANTIPSYCHOTIC SULFONAMIDE-HETEROCYCLES, AND METHODS OF USE THEREOF

(75) Inventors: Xinhe Wu, Marlborough, MA (US); Brian M. Aquila, Marlborough, MA (US); Liming Shao, Lincoln, MA (US); Heike Radeke, Dedham, MA (US); Gregory D. Cuny, Hudson, MA (US); James R. Hauske, Concord, MA (US); Roger L. Xie, Natick, MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 10/766,300

(22) Filed: Jan. 28, 2004

(65) Prior Publication Data

US 2004/0235832 A1 Nov. 25, 2004

Related U.S. Application Data

(62) Division of application No. 09/951,137, filed on Sep. 12, 2001.
(60) Provisional application No. 60/231,607, filed on Sep. 11, 2000.

(51) Int. Cl.$^7$ ...................... A61K 31/44; C07D 401/00; C07D 211/00
(52) U.S. Cl. ...................... 514/183; 514/315; 514/331; 514/277; 514/332; 514/337; 514/350; 514/354; 514/353; 514/357; 514/705; 514/603
(58) Field of Search ............................... 514/183, 315, 514/331, 277, 332, 337, 350, 354, 353, 357, 705, 603

(56) References Cited

U.S. PATENT DOCUMENTS

| | | | |
|---|---|---|---|
| 3,933,829 A | 1/1976 | Archibald et al. | 260/288 |
| 4,145,427 A | 3/1979 | Langbein et al. | 424/267 |
| 5,658,908 A | 8/1997 | Chang et al. | 514/252 |
| 3,534,049 A | 10/1997 | Bell | 260/293.4 |
| 5,703,065 A | 12/1997 | Howard, Jr. | 514/183 |
| 5,721,255 A | 2/1998 | Howard et al. | 514/329 |
| 5,854,249 A | 12/1998 | Chang et al. | 514/255 |
| 5,912,245 A | 6/1999 | Rivó et al. | 514/249 |
| 5,919,797 A | 7/1999 | Goodman et al. | 514/319 |
| 5,994,392 A | 11/1999 | Shashoua | 514/437 |
| 6,004,982 A | 12/1999 | Stupczewski et al. | 514/320 |
| 6,194,581 B1 | 2/2001 | Cosford et al. | 546/276.4 |
| 6,303,816 B1 | 10/2001 | Arnold et al. | 564/82 |
| 6,316,490 B1 | 11/2001 | Vernier et al. | 514/428 |
| 2001/0027195 A1 | 10/2001 | Nugiel et al. | 514/232.8 |

FOREIGN PATENT DOCUMENTS

| | | |
|---|---|---|
| DE | 23 47 390 | 4/1975 |
| EP | 0 481 299 A2 | 4/1992 |
| WO | 9631478 | * 10/1996 |
| WO | WO 99/47515 | 9/1999 |
| WO | 0 990 653 A1 | 4/2000 |
| WO | WO 01/64633 A1 | 9/2001 |
| WO | WO 01/64634 A1 | 9/2001 |

OTHER PUBLICATIONS

Chemical abstract DN 126:7997, also cited as WO9631478 dated Oct. 1996.*

De Paulis et al, Eur. J. Med. Chem. 25/6, 507–17(1990).*

Wise et al.; "1–[3–(Diarylmino)propyl]piperidines and Related Compounds, Potential Antipsychotic Agents With Low Cataleptogenic Profiles", J. Med. Chem. 28: 606–612 (1985).

DePaulis et al., "Potential Antipsychotic Agents", Eur. J. Med. Chem., 25/6, 507–17 (1990); also cited as Chem. Abstrct #114:190–1991: 190.

Chemical Abstract CAPLUS DN 135:288778, also cited as U.S.P. 2001027195, dated Oct. 2001.

Chemical Abstract CAPLU DN 85:21138, also cited as U.S.P. 393829, dated Jan. 1976.

Chemical Abstract CAPLUS DN 74:3525, also cited as U.S.P. 3534049, dated Oct. 1997.

PubMed Abstract 12738054, also cited as Brain Res. Brain Res. Rev. 42/2, 123–42(2003).

PubMed Abstract 12471595, also cited as Proteins, 50/1, 5–25 (2003).

International Search Report Completed on Sep. 6, 2002 and Mailed on Sep. 16, 2002.

* cited by examiner

*Primary Examiner*—Richard L. Raymond
*Assistant Examiner*—Sudhaker B. Patel
(74) *Attorney, Agent, or Firm*—Dana M. Gordon; Foley Hoag LLP

(57) ABSTRACT

One aspect of the present invention relates to heterocyclic compounds comprising a sulfonamide moiety. A second aspect of the present invention relates to the use of the heterocyclic compounds comprising a sulfonamide moiety to treat diseases, afflictions or maladies caused at least in part by abnormal activity of one or more GPCRs or ligand-gated ion channels. An additional aspect of the present invention relates to the synthesis of combinatorial libraries of the heterocyclic compounds comprising a sulfonamide moiety, and the screening of those libraries for biological activity, e.g., in animal models of psychosis.

98 Claims, No Drawings

ANTIPSYCHOTIC SULFONAMIDE-HETEROCYCLES, AND METHODS OF USE THEREOF

RELATED APPLICATIONS

This application is a division of U.S. patent application Ser. No. 09/951,137, filed Sep. 12, 2001; which claims the benefit of priority to U.S. Provisional patent application Ser. No. 60/231,607, filed Sep. 11, 2000.

BACKGROUND OF THE INVENTION

Psychiatric disorders are pathological conditions of the brain characterized by identifiable symptoms that results in abnormalities in cognition, emotion or mood, or the highest integrative aspects of behavior. These disorders may vary in severity of symptoms, duration, and functional impairment. Psychiatric disorders afflict millions of people worldwide resulting in tremendous human suffering and economic burden due to lost productivity.

Psychiatric disorders can be classified into various categories based on etiology and symptomatology. Such a classification system includes somatoform disorders, anxiety disorders, dissociative disorders, mood disorders, personality disorders, psychosexual disorders, schizophrenia and related disorders, drug abuse and dependence, and eating disorders.

In some cases the psychiatric disorder may be acute, lasting only for several weeks to months. In other instances the disorder is chronic, lasting for years or even decades. Psychiatric disorders afflict people of all ages. The initial age for onset of a psychiatric disorder also varies. For example, children may suffer attention deficit hyperactive disorder, depression and disruptive disorders. Adolescence may suffer from depression, eating disorders, and may experience the onset of schizophrenia. Other individuals may only experience psychiatric disorders in adulthood.

Like many illnesses that at one time were not well understood, psychiatric disorders may be poorly treated and seriously underestimated. Inappropriate treatment of these diseases seriously compromises the patient's quality of life, causing emotional suffering and increasing the risk of lost livelihood and disrupts social integration. In the most severe cases these disorders may lead to suicide.

Over the past several decades, the use of pharmacological agents to treat psychiatric disorders has greatly increased. The reason for this increase is largely due to research advances in both neuroscience and molecular biology. In addition, chemists have become increasingly sophisticated at creating chemical structures that are more effective therapeutic agents with fewer side effects, targeted to correct the biochemical alterations that accompany mental disorders.

The pathophysiological mechanisms responsible for psychiatric disorders are very complex. However, with increasing understanding of neuroanatomy and neurophysiology these mechanisms and the effect of pharmacological agents on these mechanisms is becoming clearer. Protein molecular targets that psychopharmaceuticals interact with to have an effect can be divided into three general classes: (1) enzymes; (2) ion channels; and (3) G-protein coupled receptors (GPCRs). The current molecular targets believed to be involved in the pathology of psychiatric disorders predominately are GPCRs. Consequently, many of the current psychotherapeutics used today are ligands for GPCRs.

Despite the many advances that occurred from a better understanding of neuropharmacology, many psychiatric diseases remain untreated or inadequately treated with current pharmaceutical agents. In addition, many of the current agents interact with molecular targets not involved with the psychiatric disease. This indiscriminate binding can result in side effects that can greatly influence the overall outcome of therapy. In some cases the side effects are so severe that discontinuation of therapy is required. Therefore, there is a current need for pharmaceutical agents that have good efficacy for the treatment of psychiatric disorders, but that have reduced side effect profiles.

Dopamine, norepinephrine and serotonin are mammalian neurotransmitters that play important roles in a wide variety of physiological processes. Therefore, compounds that selectively modulate the activity of these three neurotransmitters, either individually, in pairs, or as a group, promise to serve as agents effective in the treatment of a wide range of maladies, conditions and diseases that afflict mammals due to atypical activities of these neurotransmitters.

For example, depression is believed to result from dysfunction in the noradrenergic or serotonergic systems. Furthermore, the noradrenergic system appears to be associated with increased drive, whereas the serotonergic system relates more to changes in mood. Therefore, it is possible that the different symptoms of depression may benefit from drugs acting mainly on one or the other of these neurotransmitter systems. On the other hand, a single compound that selectively affects both the noradrenergic and serotonergic systems should prove effective in the treatment of depression comprising symptoms related to dysfunction in both systems.

Dopamine is hypothesized to play a major role in psychosis and neurodegenerative diseases. Many of the concepts that apply to dopamine apply to other neurotransmitters as well. As a chemical messenger, dopamine is similar to adrenaline. Dopamine affects brain processes that control movement, emotional response, and ability to experience pleasure and pain. Regulation of dopamine plays a crucial role in our mental and physical health. Neurons containing the neurotransmitter dopamine are clustered in the midbrain in an area called the substantia nigra. In Parkinson's disease, the dopamine-transmitting neurons in this area die. As a result, the brains of people with Parkinson's disease contain almost no dopamine. To help relieve their symptoms, these patients are given L-DOPA, a drug that can be converted in the brain to dopamine.

Certain drugs are known as dopamine agonists. These drugs bind to dopamine receptors in place of dopamine and directly stimulate those receptors. Some dopamine agonists are currently used to treat Parkinson's disease. These drugs can stimulate dopamine receptors even in someone without dopamine-secreting neurons. In contrast to dopamine agonists, dopamine antagonists are drugs that bind but don't stimulate dopamine receptors. Antagonists can prevent or reverse the actions of dopamine by keeping dopamine from attaching to receptors.

Dopamine antagonists are traditionally used to treat schizophrenia and related mental disorders. A person with schizophrenia may have an overactive dopamine system. Dopamine antagonists can help regulate this system by "turning down" dopamine activity.

Cocaine and other drugs of abuse can alter dopamine function. Such drugs may have very different actions. The specific action depends on which dopamine receptors the drugs stimulate or block, and how well they mimic dopamine. Drugs such as cocaine and amphetamine produce their effects by changing the flow of neurotransmitters. These drugs are defined as indirect acting because they depend on the activity of neurons. In contrast, some drugs bypass neurotransmitters altogether and act directly on receptors. Such drugs are direct acting.

Use of these two types of drugs can lead to very different results in treating the same disease. As mentioned earlier, people with Parkinson's disease lose neurons that contain dopamine. To compensate for this loss, the body produces more dopamine receptors on other neurons. Indirect agonists are not very effective in treating the disease since they depend on the presence of dopamine neurons. In contrast, direct agonists are more effective because they stimulate dopamine receptors even when dopamine neurons are missing.

Certain drugs increase dopamine concentrations by preventing dopamine reuptake, leaving more dopamine in the synapse. An example is methylphenidate, used therapeutically to treat childhood hyperkinesis and symptoms of schizophrenia.

Sensitization or desensitization normally occur with drug exposure. However, addiction or mental illness can tamper with the reuptake system. This disrupts the normal levels of neurotransmitters in the brain and can lead to faulty desensitization or sensitization. If this happens in a region of the brain that serves emotion or motivation, the individual can suffer severe consequences. For example, cocaine prevents dopamine reuptake by binding to proteins that normally transport dopamine. Not only does cocaine "bully" dopamine out of the way-it hangs on to the transport proteins much longer than dopamine does. As a result, more dopamine remains to stimulate neurons, which causes a prolonged feelings of pleasure and excitement. Amphetamine also increases dopamine levels. Again, the result is overstimulation of these pleasure-pathway nerves in the brain.

Dopamine activity is implicated in the reinforcing effects of cocaine, amphetamine and natural rewards. However, dopamine abnormalities are also believed to underlie some of the core attentional abnormalities seen in acute schizophrenics.

Norepinephrine, also called noradrenaline, is a neurotransmitter that doubles part-time as a hormone. As a neurotransmitter, norepinephrine helps to regulate arousal, dreaming, and moods. As a hormone, it acts to increase blood pressure, constrict blood vessels and increase heart rate—responses that occur when we feel stress.

Serotonin (5-hydroxytryptamine, 5-HT) is widely distributed in animals and plants, occurring in vertebrates, fruits, nuts, and venoms. A number of congeners of serotonin are also found in nature and have been shown to possess a variety of peripheral and central nervous system activities. Serotonin may be obtained from a variety of dietary sources; however, endogenous 5-HT is synthesized in situ from tryptophan through the actions of the enzymes tryptophan hydroxylase and aromatic L-amino acid decarboxylase. Both dietary and endogenous 5-HT are rapidly metabolized and inactivated by monoamine oxidase and aldehyde dehydrogenase to the major metabolite, 5-hydroxyindoleacetic acid (5-HIAA).

Serotonin is implicated in the etiology or treatment of various disorders, particularly those of the central nervous system, including anxiety, depression, obsessive-compulsive disorder, schizophrenia, stroke, obesity, pain, hypertension, vascular disorders, migraine, and nausea. Recently, understanding of the role of 5-HT in these and other disorders has advanced rapidly due to increasing understanding of the physiological role of various serotonin receptor subtypes.

Serotonin was first isolated from blood in 1948 by Page and coworkers and was later identified in the central nervous system. As is the case for most neurotransmitters, it has a relatively simple chemical structure but displays complex pharmacological properties. Based on the similarity of this structure to the structures of norepinephrine and dopamine, it is not surprising that serotonin, like its catecholamine counterparts, possesses a diversity of pharmacological effects, both centrally and peripherally.

Serotonin is found in three main areas of the body: the intestinal wall (where it causes increased gastrointestinal motility); blood vessels (where large vessels are constricted); and the central nervous system (CNS). The most widely studied effects of serotonin are those on the CNS. The functions of serotonin are numerous and include control of appetite, sleep, memory and learning, temperature regulation, mood, behavior (including sexual and hallucinogenic behavior), cardiovascular function, muscle contraction, endocrine regulation, and depression. Peripherally, serotonin appears to play a major role in platelet homeostasis, motility of the GI tract, and carcinoid tumor secretion. This profile represents quite a broad spectrum of pharmacological and psychological effects, considering the fact that the average human adult possesses only about 10 mg of 5-HT.

Neurotransmitters (NTs) produce their effects as a consequence of interactions with cellular receptors. Neurotransmitters, including serotonin, are synthesized in brain neurons and stored in vesicles. Upon a nerve impulse, they are released into the synaptic cleft, where they interact with various postsynaptic receptors. The actions of 5-HT are terminated by three major mechanisms: diffusion; metabolism; and uptake back into the synaptic cleft through the actions of specific amine membrane transporter systems. Thus, the actions of 5-HT, or any neurotransmitter, can be modulated by agents that: stimulate or inhibit its biosynthesis; agents that block its storage; agents that stimulate or inhibit its release; agents that mimic or inhibit its actions at its various postsynaptic receptors; agents that inhibit its reuptake into the nerve terminal; and agents that affect its metabolism.

The major mechanism by which the action of serotonin is terminated is by uptake through presynaptic membranes. After 5-HT acts on its various postsynaptic receptors, it is removed from the synaptic cleft back into the nerve terminal through an uptake mechanism involving a specific membrane transporter in a manner similar to that of other biogenic amines. Agents that selectively inhibit this uptake, i.e., membrane transporter, increase the concentration of 5-HT at the postsynaptic receptors and have been found to be quite useful in treating various psychiatric disorders, particularly depression. Approximately 5% of the U.S. population experience a depressive episode requiring psychopharmacological treatment; in any one year, 10–12 million Americans are affected by depression, with the condition twice as common in females than in males. It has been estimated that 15% of patients hospitalized for depression will commit suicide.

Depression is an affective disorder, the pathogenesis of which cannot be explained by any single cause or theory. The most widely accepted hypothesis involves abnormal function of the catecholamine (primarily norepinephrine) and/or serotonin transmitter systems. In this hypothesis, most forms of depression are associated with a deficiency of norepinephrine and/or serotonin at functionally important adrenergic or serotonergic receptors. Hence drugs that enhance the concentrations of norepinephrine (NE) and/or serotonin at these receptors should alleviate to an extent the symptoms of depression. Approaches to the treatment of depression over the years have involved the use of agents (stimulants) that mimic norepinephrine; agents (MAOIs) that increase the levels of NE and 5-HT by inhibiting their metabolism; and drugs that increase these levels at the receptor by inhibiting the uptake of NE and 5-HT.

The classical tricyclic antidepressants (TCAs) currently available block primarily the uptake of norepinephrine and also, to varying degrees, the uptake of 5-HT—depending on whether they are secondary or tertiary amines. Tertiary amines such as imipramine and amitriptyline are more selective inhibitors of 5-HT than catecholamines, compared with secondary amines such as desipramine. More recently, selective 5-HT reuptake inhibitors (SSRIs) have been investigated as potential antidepressants with the antioipation that these agents, unlike the first-generation TCAs, would possess fewer side effects, such as anticholinergic actions and cardiotoxicity, and would be less likely to cause sedation and weight gain.

Three selective 5-HT uptake inhibitors, also referred to as second-generation antidepressants, have been introduced to the U.S. market. Fluoxetine (Prozac), sertraline (Zoloft), and paroxetine (Paxil) have gained immediate acceptance, each appearing in recent listings of the top 200 prescription drugs. Fluoxetine was approved also for the treatment of obsessive-compulsive disorder. These agents do not appear to possess greater efficacy than the TCAs, nor do they generally possess a faster onset of action; however, they do have the advantage of a lower side-effect profile. Of these three SSRI, paroxetine is the most potent inhibitor of 5-HT uptake, fluoxetine the least. Sertaline is the most selective for 5-HT versus NE uptake, fluoxetine the least selective. Fluoxetine and sertraline produce active metabolites, while paroxetine is metabolized to inactive metabolites. The SSRIs, in general, affect only the uptake of serotonin and display little or no affinity for various receptor systems including muscarinic, adrenergic, dopamine, histamine, or 5-HT receptors.

In addition to treating depression, several other potential therapeutic applications for SSRIs have been investigated. They include treatment of Alzheimer's disease; modulation of aggressive behavior; treatment of premenstrual syndrome, diabetic neuropathy, and chronic pain; and suppression of alcohol intake. Of particular significance is the observation that 5-HT reduces food consumption by increasing meal-induced satiety and reducing hunger, without producing the behavioral effects of abuse liability associated with amphetamine-like drugs; thus, there is interest in the use of SSRIs in the treatment of obesity.

Venlafaxine (Effexor) is a recently introduced antidepressant, differing from the classical TCAs and the SSRIs chemically and pharmacologically in that it acts as a potent inhibitor of both 5-HT and norepinephrine uptake, as well as weakly inhibiting dopamine uptake. Its major metabolite, O-desmethylyenlafaxine, shares a similar profile. Neither venlafaxine nor its major metabolite have significant affinity for muscarinic, histaminergic, benzodiazephine, mu opioid, or adrenergic alpha-1 receptors. It is administered as a racemic mixture. Both enantiomers inhibit 5-HT and NE uptake, but the (S)(+)-isomer is more selective for 5-HT uptake. Venlafaxine possesses an efficacy equivalent to that of the TCAs, and a benign side effect profile similar to those of the SSRIs.

It is currently estimated that up to 30% of clinically diagnosed cases of depression are resistant to all forms of drug therapy. To achieve an effective therapy for such patients, it is logical to develop drugs that possess reuptake inhibition profiles different from those of drugs currently available on the market. For example, the exact role of dopamine in depressive illness is far from clear; however, intervention in the dopamine system may hold promise for the treatment of a subset of major depression.

SUMMARY OF THE INVENTION

One aspect of the present invention relates to heterocyclic compounds comprising a sulfonamide moiety. A second aspect of the present invention relates to the use of the heterocyclic compounds comprising a sulfonamide moiety to treat diseases, afflictions or maladies caused at least in part by abnormal activity of one or more GPCRs or ligand-gated ion channels. An additional aspect of the present invention relates to the synthesis of combinatorial libraries of the heterocyclic compounds comprising a sulfonamide moiety, and the screening of those libraries for biological activity, e.g., in animal models of psychosis.

DETAILED DESCRIPTION OF THE INVENTION

One aspect of the present invention relates to heterocyclic compounds comprising a sulfonamide moiety. A second aspect of the present invention relates to the use of the heterocyclic compounds comprising a sulfonamide moiety to treat psychiatric disorders, e.g., psychosis, in mammals. An additional aspect of the present invention relates to the synthesis of combinatorial libraries of the heterocyclic compounds comprising a sulfonamide moiety, and the screening of those libraries for biological activity, e.g., in animal models of psychosis.

Psychiatric disorders are pathological conditions of the brain characterized by identifiable symptoms that results in abnormalities in cognition, emotion or mood, or the highest integrative aspects of behavior. These disorders may vary in severity of symptoms, duration, and functional impairment. Psychiatric disorders afflict millions of people worldwide resulting in tremendous human suffering and economic burden due to lost productivity.

Psychiatric disorders can be classified into various categories based on etiology and symptomatology. Such a classification system includes somatoform disorders, anxiety disorders, dissociative disorders, mood disorders, personality disorders, psychosexual disorders, schizophrenia and related disorders, drug abuse and dependence, and eating disorders.

Somatoform disorders are a group of psychiatric disorders characterized by physical symptoms that suggest but are not fully explained by a physical ailment. The somatoform disorders include somatization disorder, conversion disorder, hypochondriasis, pain disorder, and body dysmorphic disorder. Somatization disorder is a chronic, severe psychiatric disorder characterized by many recurring clinically significant physical complaints (including pain, gastrointestinal, sexual, and neurologic symptoms) that cannot be explained fully by a physical ailment. Conversion disorder is a condition in which physical symptoms caused by psychological conflict are unconsciously converted to resemble those of a neurologic disorder. Hypochondriasis is a preoccupation with bodily functions and fears of acquiring or having a serious disease based on misinterpretation of physical symptoms. Pain disorder is a condition in which pain in one or more anatomic sites is exclusively or predominantly caused by psychological factors, is the main focus of the patient's attention, and results in significant distress and dysfunction. Body dysmorphic disorder is a condition in which preoccupation with a defect in appearance, causing significant distress or interfering with social, occupational, or other important areas of functioning.

Anxiety disorders are the most common class of psychiatric disorder. However, they often are not recognized and consequently not treated. Anxiety disorders may be due to a physical condition or use of a legal or illicit drug. For example, hyperthyroidism or use of corticosteroids or cocaine may produce symptoms and signs identical to those of certain primary anxiety disorders. Anxiety disorders include panic disorder, phobic disorders, obsessive-compulsive disorder, posttraumatic stress disorder, acute stress disorder, or generalized anxiety disorder. Panic disorder is characterized by sudden onset of symptoms, such as chest pain or discomfort, choking, dizziness, faintness, fear of dying, fear of going crazy or of losing control, feelings of unreality, strangeness, or detachment from the environment, flushes or chills, nausea or abdominal distress, numbness or tingling sensations, palpitations or accelerated heart rate, shortness of breath or smothering sensation, sweating, and/or trembling or shaking. Symptoms peak within 10 minutes and usually dissipate within minutes, leaving little for a physician to observe except the person's fear of another terrifying panic attack.

Phobic disorders are characterized by persistent, unrealistic, yet intense anxiety that is attached to external situations or stimuli. Obsessive-compulsive disorder is characterized by recurrent, unwanted, intrusive ideas, images, or impulses that seem silly, weird, nasty, or horrible (obsessions) and by urges to do something that will lessen the discomfort due to the obsessions (compulsions). Posttraumatic stress disorder is characterized by an overwhelming traumatic event causing intense fear, helplessness, horror, and avoidance of stimuli associated with the trauma. Acute stress disorder resembles posttraumatic stress disorder in that the person has been traumatized, reexperiences the trauma, avoids stimuli that remind him of the trauma, and has increased arousal. Generalized anxiety disorder is characterized by excessive, almost daily, anxiety and worry for more than 6 months about a number of activities or events.

Dissociative disorders are conditions involving failure to integrate one's memories, perceptions, identity, or consciousness normally. This category of conditions includes dissociative amnesia, dissociative fugue, dissociative identity disorder, and depersonalization disorder.

Mood disorders are a group of heterogeneous, typically recurrent illnesses including unipolar (depressive) and bipolar (manic-depressive) disorders that are characterized by pervasive mood disturbances, psychomotor dysfunction, and vegetative symptoms. Suicide, the most serious complication in patients with mood disorders, is the cause of death in 15 to 25% of untreated patients with mood disorders; unrecognized or inadequately treated depression contributes to 50 to 70% of all completed suicides.

Personality disorders are characterized by pervasive, inflexible, and stable personality traits that deviate from cultural norms and cause distress or functional impairment.

Psychosexual disorders include sexual dysfunction, hypoactive sexual desire disorder, sexual aversion disorder, male orgasmic disorder, gender identity disorders, transsexualism, paraphilias, fetishism, pedophilia, exhibitionism, voyeurism, sexual masochism, and sexual sadism.

Schizophrenia and related disorders have been described as among the worst diseases afflicting humankind. Schizophrenia and the related disorders including, brief psychotic disorder, schizophreniform disorder, schizoaffective disorder, and delusional disorder-are characterized by psychotic symptoms, which may include delusions, hallucinations, disorganized thinking and speech, and bizarre and inappropriate behavior. Typically, these disorders affect patients in late adolescence or early adulthood. They are often life long.

Schizophrenia is a common (about 1% worldwide) and serious mental disorder characterized by loss of contact with reality (psychosis), hallucinations (false perceptions), delusions (false beliefs), abnormal thinking, flattened affect (restricted range of emotions), diminished motivation, diminished cognitive function, and disturbed work and social functioning.

Symptoms of schizophrenia vary in type and severity. Generally they are categorized as positive or negative (deficit) symptoms. An excess or distortion of normal mental functions characterizes the positive symptoms of schizophrenia. Diminution or loss of normal functions characterizes the negative symptoms. Individual patients may have symptoms from one or both categories.

Positive symptoms can be further categorized as (1) delusions and hallucinations or (2) thought disorder and bizarre behavior. Delusions and hallucinations are sometimes referred to as the psychotic dimension of schizophrenia. Delusions are erroneous beliefs that usually involve misinterpreting experience. In persecutory delusions, the patient believes he is being tormented, followed, tricked, or spied on. In delusions of reference, the patient believes that passages from books, newspapers, song lyrics, or other environmental cues are directed at him. In delusions of thought withdrawal or thought insertion, the patient believes that others can read his mind, that his thoughts are being transmitted to others, or that thoughts and impulses are being imposed on him by outside forces. Hallucinations may occur in any sensory modality (auditory, visual, olfactory, gustatory, or tactile), but auditory hallucinations are by far the most common and characteristic of schizophrenia. The patient may hear voices commenting on his behavior, conversing with one another, or making critical and abusive comments.

Thought disorder and bizarre behavior are termed the disorganized symptom cluster. Thought disorder involves disorganized thinking, evidenced primarily by speech that is rambling, shifts from one topic to another, and is not goal directed. Speech can range from mildly disorganized to incoherent and incomprehensible. Bizarre behavior may include childlike silliness, agitation, and inappropriate appearance, hygiene, or conduct. Catatonic motor behavior is an extreme form of bizarre behavior that can include maintaining a rigid posture and resisting efforts to be moved or engaging in purposeless and unstimulated motor activity.

Negative (deficit) symptoms include blunted affect, poverty of speech, anhedonia, and associality. With blunted affect (flattening of emotions), the patient's face may appear immobile, with poor eye contact and lack of expressiveness. Poverty of speech refers to a diminution of thought reflected in decreased speech and terse replies to questions, creating the impression of inner emptiness. Anhedonia (diminished capacity to experience pleasure) may be reflected by a lack of interest in activities with substantial time spent in purposeless activity. Asociality refers to a lack of interest in relationships. Negative symptoms are often associated with a general loss of motivation and diminished sense of purpose and goals.

In some patients with schizophrenia, cognitive functioning declines, with impaired attention, abstract thinking, and problem solving. Severity of cognitive impairment is a major determinant of overall disability in these patients.

Schizophrenia is associated with about a 10% risk of suicide. Suicide is the major cause of premature death among persons with schizophrenia, and on average the disorder reduces the life span of those affected by 10 years. In addition, schizophrenia is a relatively modest risk factor for violent behavior. Threats of violence and minor aggressive outbursts are far more common than dangerous behavior occurring when a patient obeys hallucinatory voices or attacks an imagined persecutor. Very rarely, a severely depressed, isolated, paranoid person attacks or murders someone who is perceived as the single source of his difficulties (e.g., an authority, a celebrity, or his spouse).

Brief psychotic disorder is a condition in which psychotic symptoms last at least 1 day but not more than 1 month, with eventual return to normal premorbid functioning. Schizophreniform disorder is a condition with symptoms that are identical to those of schizophrenia but last only 1 to 6 months. Schizoaffective disorder is a condition characterized by significant mood symptoms (depression or mania) and symptoms of schizophrenia. Delusional disorder is the presence of one or more false beliefs that persist for at least 1 month. Delusions tend to be non-bizarre and involve situations that could occur, such as being followed, poisoned, infected, loved at a distance, or deceived by one's spouse or lover.

Drug use and dependence can be characterized as a psychiatric disorder. Two concepts contribute to the definition of drug dependence: tolerance, which describes the need to progressively increase the dose to produce the effect originally achieved with smaller doses, and physical dependence, a state of physiologic adaptation to a drug, manifested by a withdrawal (abstinence) syndrome. In a withdrawal syndrome, untoward physiologic changes occur when the drug is discontinued or its effect is blocked by a specific antagonist that displaces the agonist from its binding site on cell receptors. Physical dependence does not accompany all forms of drug dependence. Psychological dependence is accompanied by feelings of satisfaction and a desire to repeat the drug experience or to avoid the discontent of not having the drug. Drugs that cause chiefly psychological dependence include cocaine, marijuana, amphetamine, and hallucinogens, such as lysergic acid diethylamide (LSD), 3,4-methylenedioxymethamphetamine (MDMA), and peyote. Drugs that produce strong physical dependence (e.g., heroin, nicotine, and alcohol) are prone to abuse, and dependence is difficult to treat.

Eating disorders are another class of psychiatric disorders. Anorexia nervosa is characterized by a disturbed sense of body image, a morbid fear of obesity, a refusal to maintain a minimally normal body weight, and, in women, amenorrhea. Bulimia nervosa is another disorder characterized by recurrent episodes of binge eating during which the patient consumes large amounts of food and feels unable to stop eating, followed by inappropriate compensatory efforts to avoid weight gain, such as self-induced vomiting, laxative or diuretic abuse, vigorous exercise, or fasting. Binge eating disorder is characterized by bingeing not followed by purging.

Over the past several decades, the use of pharmacological agents to treat psychiatric disorders has greatly increased. The reason for this increase is largely due to research advances in both neuroscience and molecular biology. In addition, chemists have become increasingly sophisticated at creating chemical structures that are more effective therapeutic agents with fewer side effects, targeted to correct the biochemical alterations that accompany mental disorders.

The pathophysiological mechanisms responsible for psychiatric disorders are very complex. However, with increasing understanding of neuroanatomy and neurophysiology these mechanisms and the effect of pharmacological agents on these mechanisms is becoming clearer. Protein molecular targets that psychopharmaceuticals interact with to have an effect can be divided into three general classes: (1) enzymes; (2) ion channels; and (3) G-protein coupled receptors (GPCRs). The current molecular targets believed to be involved in the pathology of psychiatric disorders predominately are GPCRs. Consequently, many of the psychotherapeutics used today are ligands for GPCRs.

Despite the many advances that occurred from a better understanding of neuropharmacology, many psychiatric diseases remain untreated or inadequately treated with current pharmaceutical agents. In addition, many of the current agents interact with molecular targets not involved with the psychiatric disease. This indiscriminate binding can result in side effects that can greatly influence the overall outcome of therapy. In some cases the side effects are so severe that discontinuation of therapy is required.

Research into the development of new, selective ligands for neuronal GPCRs or ligand-gated ion channels holds the promise of yielding potent compounds for the treatment of psychiatric disorders that lack the side effects of current therapies. Individual compounds described herein promise to have agonistic, antagonistic, and hybrid effects on GPCRs, ligand-gated ion channels, and other cellular receptors. One aspect of the present invention relates to the use of compounds of the present invention to treat diseases, afflictions, or maladies caused, at least in part, by abnormal activity of one or more GPCRs or ligand-gated ion channels, such as but not limited to, N-methyl-D-aspartic acid, serotonin, dopamine, and norephedrine receptors. Additionally, new compounds reported herein may possess properties for treating psychiatric disorders, stroke, senile dementia, Parkinson's disease, and other neurological conditions free of side effects encountered with currently available therapies.

Certain cell surface proteins permit intracellular transduction of extracellular signals. These cell surface proteins provide eukaryotic and prokaryotic cells a means to detect extracellular signals and transduce such signals intracellularly in a manner that ultimately results in a cellular response or a concerted tissue or organ response. Moreover, these cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as growth hormones, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals, indirectly alter gene expression by activating the expression of genes, such as immediate-early genes that encode regulatory proteins, which in turn activate expression of other genes that encode transcriptional regulatory proteins. For example, neuron gene expression is modulated by numerous extracellular signals, including neurotransmitters and membrane electrical activity. Transsynaptic signals cause rapid responses in neurons that occur over a period of time ranging from milliseconds, such as the opening of ligand-gated channels, to seconds and minutes, such as second messenger-mediated events. Genes in neural cells that are responsive to transsynaptic stimulation and membrane electrical activity, include genes, called immediate early genes, whose transcription is activated rapidly, within minutes, and transiently (see, e.g., Sheng et al. (1990) Neuron 4: 477–485), and genes whose expression requires protein synthesis and whose expression is induced or altered over the course of hours.

Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Cell surface-localized receptors are membrane spanning proteins that bind extracellular signalling molecules or changes in the extracellular environment and transmit the signal via signal transduction pathways to effect a cellular response. Cell surface receptors bind circulating signal polypeptides, such as neurotransmitters, growth factors and hormones, as the initiating step in the induction of numerous intracellular pathways. Receptors are classified on the basis of the particular type of pathway that is induced. Included among these classes of receptors are those that bind growth factors and have intrinsic tyrosine kinase activity, such as the heparin binding growth factor (HBGF) receptors, and those that couple to effector proteins through guanine nucleotide binding regulatory proteins, which are referred to as G protein coupled receptors and G proteins, respectively.

The G protein transmembrane signaling pathways consist of three proteins: receptors, G proteins and effectors. G proteins, which are the intermediaries in transmembrane signaling pathways, are heterodimers and consist of alpha, beta and gamma subunits. Among the members of a family of G proteins the alpha subunits differ. Functions of G proteins are regulated by the cyclic association of GTP with the alpha subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

G protein-coupled receptors, which are glycoproteins, are known to share certain structural similarities and homologies (see, e-g., Gilman, A. G., Ann. Rev. Biochem.56: 615–649 (1987), Strader, C. D. et al. The FASEB Journal 3: 1825–1832 (1989), Kobilka, B. K., et al. Nature 329:75–79 (1985) and Young et al. Cell 45: 711–719 (1986)). Among the G protein-coupled receptors that have been identified and cloned are the substance P receptor, the angiotensin receptor, the alpha—and beta—adrenergic receptors and the serotonin receptors. G protein-coupled receptors share a conserved structural motif. The general and common structural features of the G protein-coupled receptors are the existence of seven hydrophobic stretches of about 20–25 amino acids each surrounded by eight hydrophilic regions of variable length. It has been postulated that each of the seven hydrophobic regions forms a transmembrane alpha helix and the intervening hydrophilic regions form alternately intracellularly and extracellularly exposed loops. The third cytosolic loop between transmembrane domains five and six is the intracellular domain responsible for the interaction with G proteins.

G protein-coupled receptors are known to be inducible. This inducibility was originally described in lower eukaryotes. For example, the cAMP receptor of the cellular slime mold, Dictyostelium, is induced during differentiation (Klein et al., Science 241: 1467–1472 (1988). During the Dictyostelium discoideum differentiation pathway, cAMP, induces high level expression of its G protein-coupled receptor. This receptor transduces the signal to induce the expression of the other genes involved in chemotaxis, which permits multicellular aggregates to align, organize and form stalks (see, Firtel, R. A., et al. Cell 58: 235–239 (1989) and Devreotes, P., Science 245: 1054–1058 (1989)).

Definitions

For convenience, certain terms employed in the specification, examples, and appended claims are collected here.

The term "cell surface proteins" includes molecules that occur on the surface of cells, interact with the extracellular environment, and transmit or transduce information regarding the environment intracellularly.

The term "extracellular signals" includes a molecule or a change in the environment that is transduced intracellularly via cell surface proteins that interact, directly or indirectly, with the signal. An extracellular signal is any compound or substance that in some manner specifically alters the activity of a cell surface protein. Examples of such signals include, but are not limited to, molecules such as acetylcholine, growth factors, hormones and other mitogenic substances, such as phorbol mistric acetate (PMA), that bind to cell surface receptors and ion channels and modulate the activity of such receptors and channels. Extracellular signals also includes as yet unidentified substances that modulate the activity of a cell surface protein and thereby affect intracellular functions and that are potential pharmacological agents that may be used to treat specific diseases by modulating the activity of specific cell surface receptors.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1-C_{30}$ for straight chain, $C_3-C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, or the like. The temm "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The terms "amine" and "amino" are art-recognized and refer to both unsubstituted and substituted amines, e.g., a moiety that can be represented by the general formula:

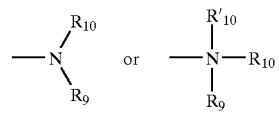

wherein $R_9$, $R_{10}$ and $R'_{10}$ each independently represent a group permitted by the rules of valence.

The term "acylamino" is art-recognized and refers to a moiety that can be represented by the general formula:

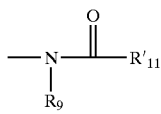

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

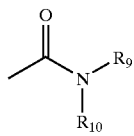

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

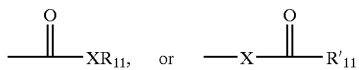

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

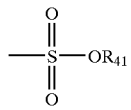

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

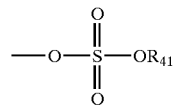

in which $R_{41}$ is as defined above.

The term "sulfonylamino" is art recognized and includes a moiety that can be represented by the general formula:

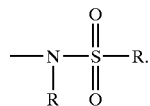

The term "sulfamoyl" is art-recognized and includes a moiety that can be represented by the general formula:

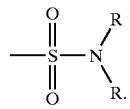

The term "sulfonyl", as used herein, refers to a moiety that can be represented by the general formula:

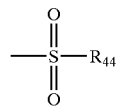

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

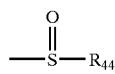

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se-$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Compounds of the Invention

In certain embodiments, a compound of the present invention is represented by A:

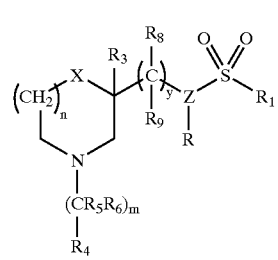

wherein
X represents $C(R_3)_2$, O, S, SO, $SO_2$, $NR_2$, $NC(O)R_1$, $NC(O)OR_2$, $NS(O)_2R_1$, or C=O;
Z represents N or CR;
m is 0, 1, 2, 3 or 4;
n is 1 or 2;
p is 1, 2, or 3;
y is 0, 1, or 2;
R represents H, alkyl, cycloalkyl, aryl, heteroaryl, aralkyl, or heteroaralkyl;
$R_1$ represents $NR_2$, alkyl, cycloalkyl, aryl, heteroaryl, aralkyl, or heteroaralkyl;
R and $R_1$ may be connected through a covalent bond;
$R_2$ represents independently for each occurrence H, alkyl, fluoroalkyl, aryl, heteroaryl, or cycloalkyl;

$R_3$ represents independently for each occurrence H, alky, aryl, $OR_2$, $OC(O)R_2$, $CH_2OR_2$, or $CO_2R_2$; wherein any two instances of $R_3$ may be connected by a covalent tether whose backbone consists of 1, 2, 3, or 4 carbon atoms;

$R_4$ represents independently for each occurrence H, alkyl, aryl, heteroaryl, alkenyl, or cycloalkyl;

$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is $C(O)$;

$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8R_9$ taken together is $C(O)$;

Y represents independently for each occurrence $OR_2$, $N(R_2)_2$, $SR_2$, $S(O)R_2$, $S(O)_2R_2$, or $P(O)(OR_2)_2$;

any two instances of $R_2$ may be connected through a covalent bond;

a covalent bond may connect $R_4$ and an instance of $R_5$ or $R_6$;

any two instances of $R_5$ and $R_6$ may be connected through a covalent bond;

any two geminal or vicinal instances of $R_8$ and $R_9$ may be connected through a covalent bond; and the stereochemical configuration at any stereocenter of a compound represented by A is R, S, or a mixture of these configurations.

In certain embodiments, the compounds of the present invention are represented by A and the attendant definitions, wherein X is $C(R_3)_2$, O, or $NR_2$.

In certain embodiments, the compounds of the present invention are represented by A and the attendant definitions, wherein X is $C(R_3)_2$.

In certain embodiments, the compounds of the present invention are represented by A and the attendant definitions, wherein m is 2.

In certain embodiments, the compounds of the present invention are represented by A and the attendant definitions, wherein n is 1.

In certain embodiments, the compounds of the present invention are represented by A and the attendant definitions, wherein y is 1.

In certain embodiments, the compounds of the present invention are represented by A and the attendant definitions, wherein $R_1$ represents aryl or heteroaryl.

In certain embodiments, the compounds of the present invention are represented by A and the attendant definitions, wherein $R_1$ represents alkyl or aryl.

In certain embodiments, the compounds of the present invention are represented by A and the attendant definitions, wherein $R_3$ represents independently for each occurrence H or alkyl.

In certain embodiments, the compounds of the present invention are represented by A and the attendant definitions, wherein $R_4$ represents cycloalkyl, aryl, or heteroaryl.

In certain embodiments, the compounds of the present invention are represented by A and the attendant definitions, wherein $R_5$ and $R_6$ are selected independently for each occurrence from the group consisting of H, alkyl, $OR_2$, aryl, heteroaryl, and F.

In certain embodiments, the compounds of the present invention are represented by A and the attendant definitions, wherein $R_8$ and $R_9$ are selected independently for each occurrence from the group consisting of H, alkyl, $OR_2$, aryl, heteroaryl, and F.

In certain embodiments, the compounds of the present invention are represented by A and the attendant definitions, wherein X is $C(R_3)_2$; and m is 2.

In certain embodiments, the compounds of the present invention are represented by A and the attendant definitions, wherein X is $C(R_3)_2$; and n is 1.

In certain embodiments, the compounds of the present invention are represented by A and the attendant definitions, wherein X is $C(R_3)_2$; and y is 1.

In certain embodiments, the compounds of the present invention are represented by A and the attendant definitions, wherein X is $C(R_3)_2$; m is 2; n is 1; and y is 1.

In certain embodiments, the compounds of the present invention are represented by A and the attendant definitions, wherein X is $C(R_3)_2$; m is 2; n is 1; y is 1; and R is aryl or heteroaryl.

In certain embodiments, the compounds of the present invention are represented by A and the attendant definitions, wherein X is $C(R_3)_2$; m is 2; n is 1; y is 1; R is aryl or heteroaryl; and $R_1$ represents alkyl or aryl.

In certain embodiments, the compounds of the present invention are represented by A and the attendant definitions, wherein X is $C(R_3)_2$; m is 2; n is 1; y is 1; R is aryl or heteroaryl; $R_1$ represents alkyl or aryl; and $R_3$ represents independently for each occurrence H or alkyl.

In certain embodiments, the compounds of the present invention are represented by A and the attendant definitions, wherein X is $C(R_3)_2$; m is 2; n is 1; y is 1; R is aryl or heteroaryl; $R_1$ represents alkyl or aryl; $R_3$ represents independently for each occurrence H or alkyl; and $R_4$ represents cycloalkyl, aryl, or heteroaryl.

In certain embodiments, the compounds of the present invention are represented by A and the attendant definitions, wherein X is $C(R_3)_2$; m is 2; n is 1; y is 1; R is aryl or heteroaryl; $R_1$ represents alkyl or aryl; $R_3$ represents independently for each occurrence H or alkyl; $R_4$ represents cycloalkyl, aryl, or heteroaryl; and $R_5$ and $R_6$ are selected independently for each occurrence from the group consisting of H, alkyl, $OR_2$, aryl, heteroaryl, and F.

In certain embodiments, the compounds of the present invention are represented by A and the attendant definitions, wherein X is $C(R_3)_2$; m is 2; n is 1; y is 1; R is aryl or heteroaryl; $R_1$ represents alkyl or aryl; $R_3$ represents independently for each occurrence H or alkyl; $R_4$ represents cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

In an assay based on a mammalian GPCR or ligand-gated ion channel, certain compounds according to structure A have $IC_{50}$ values less than 1 μM, more preferably less than 100 nM, and most preferably less than 10 nM.

In an assay based on a mammalian GPCR, certain compounds according to structure A have $IC_{50}$ values less than 1 μM, more preferably less than 100 nM, and most preferably less than 10 nM.

In certain embodiments, a compound of the present invention is represented by B:

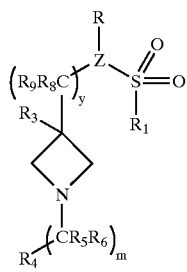

wherein
Z represents N or CR;
m is 0, 1, 2, 3 or 4;
p is 1, 2, or 3;
y is 0, 1 or 2;
R represents H, alkyl, cycloalkyl, aryl, heteroaryl, aralkyl, or heteroaralkyl;
$R_1$ represents $NR_2$, alkyl, cycloalkyl, aryl, heteroaryl, aralkyl, or heteroaralkyl;
R and $R_1$ may be connected through a covalent bond;
$R_2$ represents independently for each occurrence H, alkyl, fluoroalkyl, aryl, heteroaryl, or cycloalkyl;
$R_3$ represents independently for each occurrence H, alkyl, aryl, $OR_2$, $OC(O)R_2$, $CH_2OR_2$, or $CO_2R_2$;
$R_4$ represents H, alkyl, aryl, heteroaryl, alkenyl, or cycloalkyl;
$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is $C(O)$;
$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8R_9$ taken together is $C(O)$;
Y represents independently for each occurrence $OR_2$, $N(R_2)_2$, $SR_2$, $S(O)R_2$, $S(O)_2R_2$, or $P(O)(OR_2)_2$;
any two instances of $R_2$ may be connected through a covalent bond;
a covalent bond may connect $R_4$ and an instance of $R_5$ or $R_6$;
any two instances of $R_5$ and $R_6$ may be connected through a covalent bond;
any two geminal or vicinal instances of $R_8$ and $R_9$ may be connected through a covalent bond; and
the stereochemical configuration at any stereocenter of a compound represented by B is R, S, or a mixture of these configurations.

In certain embodiments, the compounds of the present invention are represented by B and the attendant definitions, wherein m is 2.

In certain embodiments, the compounds of the present invention are represented by B and the attendant definitions, wherein y is 1.

In certain embodiments, the compounds of the present invention are represented by B and the attendant definitions, wherein R represents aryl or heteroaryl.

In certain embodiments, the compounds of the present invention are represented by B and the attendant definitions, wherein $R_1$ represents alkyl or aryl.

In certain embodiments, the compounds of the present invention are represented by B and the attendant definitions, wherein $R_3$ represents independently for each occurrence H or alkyl.

In certain embodiments, the compounds of the present invention are represented by B and the attendant definitions, wherein $R_4$ represents cycloalkyl, aryl, or heteroaryl.

In certain embodiments, the compounds of the present invention are represented by B and the attendant definitions, wherein $R_5$ and $R_6$ are selected independently for each occurrence from the group consisting of H, alkyl, $OR_2$, aryl, heteroaryl, and F.

In certain embodiments, the compounds of the present invention are represented by B and the attendant definitions, wherein $R_8$ and $R_9$ are selected independently for each occurrence from the group consisting of H, alkyl, $OR_2$, aryl, heteroaryl, and F.

In certain embodiments, the compounds of the present invention are represented by B and the attendant definitions, wherein m is 2; and y is 1.

In certain embodiments, the compounds of the present invention are represented by B and the attendant definitions, wherein m is 2; y is 1; and R represents aryl or heteroaryl.

In certain embodiments, the compounds of the present invention are represented by B and the attendant definitions, wherein m is 2; y is 1; R represents aryl or heteroaryl; and $R_1$ represents alkyl or aryl.

In certain embodiments, the compounds of the present invention are represented by B and the attendant definitions, wherein m is 2; y is 1; R represents aryl or heteroaryl; $R_1$ represents alkyl or aryl; and $R_3$ represents independently for each occurrence H or alkyl.

In certain embodiments, the compounds of the present invention are represented by B and the attendant definitions, wherein m is 2; y is 1; R represents aryl or heteroaryl; $R_1$ represents alkyl or aryl; $R_3$ represents independently for each occurrence H or alkyl; and $R_4$ represents cycloalkyl, aryl, or heteroaryl.

In certain embodiments, the compounds of the present invention are represented by B and the attendant definitions, wherein m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; and $R_5$ and $R_6$ are selected independently for each occurrence from the group consisting of H, alkyl, $OR_2$, aryl, heteroaryl, and F.

In certain embodiments, the compounds of the present invention are represented by B and the attendant definitions, wherein m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

In an assay based on a mammalian GPCR or ligand-gated ion channel, certain compounds according to structure B have $IC_{50}$ values less than 1 $\mu$M, more preferably less than 100 nM, and most preferably less than 10 nM.

In an assay based on a mammalian GPCR, certain compounds according to structure B have $IC_{50}$ values less than 1 $\mu$M, more preferably less than 100 nM, and most preferably less than 10 nM.

In certain embodiments, a compound of the present invention is represented by C:

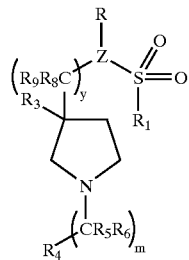

wherein
- Z represents N or CR;
- m is 0, 1, 2, 3 or 4;
- p is 1, 2, or 3;
- y is 0, 1 or 2;
- R represents H, alky, cycloalkyl, aryl, heteroaryl, aralkyl, or heteroaralkyl;
- $R_1$ represents $NR_2$, alkyl, cycloalkyl, aryl, heteroaryl, aralkyl, or heteroaralkyl;
- R and $R_1$ may be connected through a covalent bond;
- $R_2$ represents independently for each occurrence H, alkyl, fluoroalkyl, aryl, heteroaryl, or cycloalkyl;
- $R_3$ represents independently for each occurrence H, alkyl, aryl, $OR_2$, $OC(O)R_2$, $CH_2OR_2$, or $CO_2R_2$;
- $R_4$ represents H, alkyl, aryl, heteroaryl, alkenyl, or cycloalkyl;
- $R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is C(O);
- $R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8R_9$ taken together is C(O);
- Y represents independently for each occurrence $OR_2$, $N(R_2)_2$, $SR_2$, $S(O)R_2$, $S(O)_2R_2$, or $P(O)(OR_2)_2$;
- any two instances of $R_2$ may be connected through a covalent bond;
- a covalent bond may connect $R_4$ and an instance of $R_5$ or $R_6$;
- any two instances of $R_5$ and $R_6$ may be connected through a covalent bond;
- any two geminal or vicinal instances of $R_8$ and $R_9$ may be connected through a covalent bond; and
- the stereochemical configuration at any stereocenter of a compound represented by C is R or S, or a mixture of these configurations.

In certain embodiments, the compounds of the present invention are represented by C and the attendant definitions, wherein m is 2.

In certain embodiments, the compounds of the present invention are represented by C and the attendant definitions, wherein y is 1.

In certain embodiments, the compounds of the present invention are represented by C and the attendant definitions, wherein R represents aryl or heteroaryl.

In certain embodiments, the compounds of the present invention are represented by C and the attendant definitions, wherein $R_1$ represents alkyl or aryl.

In certain embodiments, the compounds of the present invention are represented by C and the attendant definitions, wherein $R_3$ represents independently for each occurrence H or alkyl.

In certain embodiments, the compounds of the present invention are represented by C and the attendant definitions, wherein $R_4$ represents cycloalkyl, aryl, or heteroaryl.

In certain embodiments, the compounds of the present invention are represented by C and the attendant definitions, wherein $R_5$ and $R_6$ are selected independently for each occurrence from the group consisting of H, alkyl, $OR_2$, aryl, heteroaryl, and F.

In certain embodiments, the compounds of the present invention are represented by C and the attendant definitions, wherein $R_8$ and $R_9$ are selected independently for each occurrence from the group consisting of H, alkyl, $OR_2$, aryl, heteroaryl, and F.

In certain embodiments, the compounds of the present invention are represented by C and the attendant definitions, wherein m is 2; and y is 1.

In certain embodiments, the compounds of the present invention are represented by C and the attendant definitions, wherein m is 2; y is 1; and R represents aryl or heteroaryl.

In certain embodiments, the compounds of the present invention are represented by C and the attendant definitions, wherein m is 2; y is 1; R represents aryl or heteroaryl; and $R_1$ represents alkyl or aryl.

In certain embodiments, the compounds of the present invention are represented by C and the attendant definitions, wherein m is 2; y is 1; R represents aryl or heteroaryl; $R_1$ represents alkyl or aryl; and $R_3$ represents independently for each occurrence H or alkyl.

In certain embodiments, the compounds of the present invention are represented by C and the attendant definitions, wherein m is 2; y is 1; R represents aryl or heteroaryl; $R_1$ represents alkyl or aryl; $R_3$ represents independently for each occurrence H or alkyl; and $R_4$ represents cycloalkyl, aryl, or heteroaryl.

In certain embodiments, the compounds of the present invention are represented by C and the attendant definitions, wherein m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; and $R_5$ and $R_6$ are selected independently for each occurrence from the group consisting of H, alkyl, $OR_2$, aryl, heteroaryl, and F.

In certain embodiments, the compounds of the present invention are represented by C and the attendant definitions, wherein m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

In an assay based on a mammalian GPCR or ligand-gated ion channel, certain compounds according to structure C have $IC_{50}$ values less than 1 $\mu$M, more preferably less than 100 nM, and most preferably less than 10 nM.

In an assay based on a mammalian GPCR, certain compounds according to structure C have $IC_{50}$ values less than 1 $\mu$M, more preferably less than 100 nM, and most preferably less than 10 nM.

In certain embodiments, a compound of the present invention is represented by D:

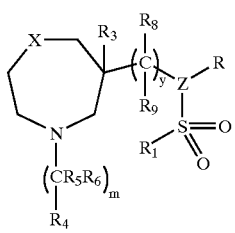

wherein
X represents $C(R_3)_2$, O, S, SO, $SO_2$, $NR_2$, $NC(O)R_1$, $NC(O)OR_2$, $NS(O)_2R_1$, or C=O;
Z represents N or CR;
m is 0, 1, 2, 3 or 4;
p is 1, 2, or 3;
y is 0, 1, or 2;
R represents H, alkyl, cycloalkyl, aryl, heteroaryl, aralkyl, or heteroaralkyl;
$R_1$ represents $NR_2$, alkyl, cycloalkyl, aryl, heteroaryl, aralkyl, or heteroaralkyl;
R and $R_1$ may be connected through a covalent bond;
$R_2$ represents independently for each occurrence H, alkyl, fluoroalkyl, aryl, heteroaryl, or cycloalkyl;
$R_3$ represents independently for each occurrence H, alkyl, aryl, $OR_2$, $OC(O)R_2$, $CH_2OR_2$, or $CO_2R_2$;
$R_4$ represents independently for each occurrence H, alkyl, aryl, heteroaryl, alkenyl, or cycloalkyl;
$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_8R_6$ taken together is $C(O)$;
$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8R_9$ taken together is $C(O)$;
Y represents independently for each occurrence $OR_2$, $N(R_2)_2$, $SR_2$, $S(O)R_2$, $S(O)_2R_2$, or $P(O)(OR_2)_2$;
any two instances of $R_2$ may be connected through a covalent bond;
a covalent bond may connect $R_4$ and an instance of $R_5$ or $R_6$;
any two instances of $R_5$ and $R_6$ may be connected through a covalent bond;
any two geminal or vicinal instances of $R_8$ and $R_9$ may be connected through a covalent bond; and
the stereochemical configuration at any stereocenter of a compound represented by D is R, S, or a mixture of these configurations.

In certain embodiments, the compounds of the present invention are represented by D and the attendant definitions, wherein X is O or $NR_2$.

In certain embodiments, the compounds of the present invention are represented by D and the attendant definitions, wherein m is 2.

In certain embodiments, the compounds of the present invention are represented by D and the attendant definitions, wherein y is 1.

In certain embodiments, the compounds of the present invention are represented by D and the attendant definitions, wherein R represents aryl or heteroaryl.

In certain embodiments, the compounds of the present invention are represented by D and the attendant definitions, wherein $R_1$ represents alkyl or aryl.

In certain embodiments, the compounds of the present invention are represented by D and the attendant definitions, wherein $R_3$ represents independently for each occurrence H or alkyl.

In certain embodiments, the compounds of the present invention are represented by D and the attendant definitions, wherein $R_4$ represents cycloalkyl, aryl, or heteroaryl.

In certain embodiments, the compounds of the present invention are represented by D and the attendant definitions, wherein $R_5$ and $R_6$ are selected independently for each occurrence from the group consisting of H, alkyl, $OR_2$, aryl, heteroaryl, and F.

In certain embodiments, the compounds of the present invention are represented by D and the attendant definitions, wherein $R_8$ and $R_9$ are selected independently for each occurrence from the group consisting of H, alky, $OR_2$, aryl, heteroaryl, and F.

In certain embodiments, the compounds of the present invention are represented by D and the attendant definitions, wherein X is O or $NR_2$; and m is 2.

In certain embodiments, the compounds of the present invention are represented by D and the attendant definitions, wherein X is O or $NR_2$; and y is 1.

In certain embodiments, the compounds of the present invention are represented by D and the attendant definitions, wherein X is O or $NR_2$; m is 2; and y is 1.

In certain embodiments, the compounds of the present invention are represented by D and the attendant definitions, wherein X is O or $NR_2$; m is 2; y is 1; and R represents aryl or heteroaryl.

In certain embodiments, the compounds of the present invention are represented by D and the attendant definitions, wherein X is O or $NR_2$; m is 2; y is 1; R represents aryl or heteroaryl; and $R_1$ represents alkyl or aryl.

In certain embodiments, the compounds of the present invention are represented by D and the attendant definitions, wherein X is O or $NR_2$; m is 2; y is 1; R represents aryl or heteroaryl; $R_1$ represents alkyl or aryl; and $R_3$ represents independently for each occurrence H or alkyl.

In certain embodiments, the compounds of the present invention are represented by D and the attendant definitions, wherein X is O or $NR_2$; m is 2; y is 1; R represents aryl or heteroaryl; $R_1$ represents alkyl or aryl; $R_3$ represents independently for each occurrence H or alkyl; and $R_4$ represents cycloalkyl, aryl, or heteroaryl.

In certain embodiments, the compounds of the present invention are represented by D and the attendant definitions, wherein X is O or $NR_2$; m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; and $R_5$ and $R_6$ are selected independently for each occurrence from the group consisting of H, alkyl, $OR_2$, aryl, heteroaryl, and F.

In certain embodiments, the compounds of the present invention are represented by D and the attendant definitions, wherein X is O or $NR_2$; m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

In an assay based on a mammalian GPCR or ligand-gated ion channel, certain compounds according to structure D have $IC_{50}$ values less than 1 $\mu$M, more preferably less than 100 nM, and most preferably less than 10 nM.

In an assay based on a mammalian GPCR, certain compounds according to structure D have $IC_{50}$ values less than 1 μM, more preferably less than 100 nM, and most preferably less than 10 nM.

In certain embodiments, the present invention relates to a compound represented by any of the structures outlined above, wherein said compound is a single stereoisomer.

In certain embodiments, the present invention relates to a formulation, comprising a compound represented by any of the structures outlined above; and a pharmaceutically acceptable excipient.

In certain embodiments, the present invention relates to a method of treating a psychiatric disorder in a mammal, comprising the step of administering to said mammal a therapeutically effective amount of a compound of the present invention. In certain embodiments of this method, said psychiatric disorder is a psychosis. In other embodiments of this method, said psychiatric disorder is schizophrenia. In other embodiments of this method, said psychiatric disorder is paranoia, manic depression, or depression. In certain embodiments of this method, said mammal is a primate, equine, canine or feline. In other embodiments of this method, said mammal is a human. In certain embodiments of this method, said compound is administered orally. In other embodiments of this method, said compound is administered intravenously. In other embodiments of this method, said compound is administered sublingually. In other embodiments of this method, said compound is administered intramuscularly.

In certain embodiments, the present invention relates to a method of treating a mammal suffering from an anxiety disorder, a dissociative disorder, a mood disorder, a personality disorder, a psychosexual disorder, an eating disorder, drug addiction or dependence, depression, manic depression, paranoia, psychosis, schizophrenia, or inflammatory pain, comprising the step of administering to said mammal a therapeutically effective amount of a compound of the present invention. In certain embodiments of this method, said mammal is a primate, equine, canine or feline. In other embodiments of this method, said mammal is a human. In certain embodiments of this method, said compound is administered orally. In other embodiments of this method, said compound is administered intravenously. In other embodiments of this method, said compound is administered sublingually. In other embodiments of this method, said compound is administered intramuscularly.

In certain embodiments, the present invention relates to ligands for transporters of neurotransmitters, e.g., dopamine, norepinephrine, and/or serotonin, wherein the ligands are represented by any of the structures outlined above, and any of the sets of definitions associated with one of those structures. In certain embodiments, the ligands of the present invention are antagonists or agonists of transporters of neurotransmitters. In any event, the ligands of the present invention preferably exert their effect on the neurotransmitter transporters at a concentration less than about 1 micromolar, more preferably at a concentration less than about 100 nanomolar, and most preferably at a concentration less than 10 nanomolar.

In certain embodiments, the selectivity of a ligand for neurotransmitter transporters renders that ligand an effective therapeutic agent for an acute or chronic ailment, disease or malady. In certain embodiments, the selectivity of a ligand for a specific neurotransmitter transporter consists of a binding affinity for that transporter at least a factor of ten greater than its binding affinity for transporters of other neurotransmitters. In certain embodiments, the selectivity of a ligand for a specific neurotransmitter transporter consists of a binding affinity for that transporter at least a factor of one hundred greater than its binding affinity for transporters of other neurotransmitters. In certain embodiments, the selectivity of a ligand for a specific neurotransmitter transporter consists of a binding affinity for that transporter at least a factor of one thousand greater than its binding affinity for transporters of other neurotransmitters.

In certain embodiments, the present invention relates to ligands for G-protein-coupled receptors, wherein the ligands are represented by any of the structures outlined above, and any of the sets of definitions associated with one of those structures. Preferably the ligands of the present invention are antagonists or agonists of the G-protein-coupled receptors. In any event, the ligands of the present invention preferably exert their effect on the receptors at a concentration less than about 1 micromolar, more preferably at a concentration less than about 100 nanomolar, and most preferably at a concentration less than 10 nanomolar. In certain embodiments, the ligands of the present invention bind selectively to a single family of G-protein-coupled receptors, e.g., the family of norepinephrine, or sigma receptors. In other embodiments, the ligands of the present invention bind selectively to a subtype of receptor within a family of G-protein-coupled receptors, e.g., the sigma-1 receptor subtype.

In certain embodiments, the selectivity of a ligand for a specific family or subtype of receptor renders that ligand an effective therapeutic agent for an acute or chronic ailment, disease or malady. In certain embodiments, the selectivity of a ligand for a specific family or subtype of receptor consists of a binding affinity for that family or subtype of receptor at least a factor of ten greater than its binding affinity for other families or subtypes of G-protein-coupled receptors. In preferred embodiments, the selectivity of a ligand for a specific family or subtype of receptor consists of a binding affinity for that family or subtype of receptor at least a factor of one hundred greater than its binding affinity for other families or subtypes of G-protein-coupled receptors. In certain embodiments, the selectivity of a ligand for a specific family or subtype of receptor consists of a binding affinity for that family or subtype of receptor at least a factor of one thousand greater than its binding affinity for other families or subtypes of G-protein-coupled receptors.

The present invention contemplates pharmaceutical formulations of the ligands of the present invention. In certain embodiments, the pharmaceutical formulations will comprise ligands of the present invention that are selective for a specific neurotransmitter transporter, and thereby have a therapeutic effect on an acute or chronic ailment, disease or malady that is at least in part due to biochemical or physiological processes associated with that neurotransmitter or transporter thereof. The Background of the Invention (see above) teaches examples of acute or chronic ailments, diseases or maladies that are caused or exacerbated by biochemical or physiological processes associated with neurotransmitter transporters. One of ordinary skill in the art will be able to accumulate, by reference to the scientific literature, a more comprehensive list of acute or chronic ailments, diseases or maladies that are caused or exacerbated by biochemical or physiological processes associated with neurotransmitter transporters. The present invention contemplates pharmaceutical formulations of ligands of the present invention that will be of medicinal value against the aforementioned acute or chronic ailments, diseases or maladies.

Biochemical Activity at Cellular Receptors, and Assays to Detect That Activity

Assaying processes are well known in the art in which a reagent is added to a sample, and measurements of the sample and reagent are made to identify sample attributes stimulated by the reagent. For example, one such assay process concerns determining in a chromogenic assay the amount of an enzyme present in a biological sample or solution. Such assays are based on the development of a colored product in the reaction solution. The reaction develops as the enzyme catalyzes the conversion of a colorless chromogenic substrate to a colored product.

Another assay useful in the present invention concerns determining the ability of a ligand to bind to a biological receptor utilizing a technique well known in the art referred to as a radioligand binding assay. This assay accurately determines the specific binding of a radioligand to a targeted receptor through the delineation of its total and nonspecific binding components. Total binding is defined as the amount of radioligand that remains following the rapid separation of the radioligand bound in a receptor preparation (cell homogenates or recombinate receptors) from that which is unbound. The nonspecific binding component is defined as the amount of radioligand that remains following separation of the reaction mixture consisting of receptor, radioligand and an excess of unlabeled ligand. Under this condition, the only radioligand that remains represents that which is bound to components other that receptor. The specific radioligand bound is determined by subtracting the nonspecific from total radioactivity bound. For a specific example of radioligand binding assay for 1-opioid receptor, see Wang, J. B. et al. *FEBS Letters* 1994, 338, 217.

Assays useful in the present invention concern determining the activity of receptors the activation of which initiates subsequent intracellular events in which intracellular stores of calcium ions are released for use as a second messenger. Activation of some G-protein-coupled receptors stimulates the formation of inositol triphosphate (IP3, a G-protein-coupled receptor second messenger) through phospholipase C-mediated hydrolysis of phosphatidylinositol, Berridge and Irvine (1984). Nature 312:315–21. IP3 in turn stimulates the release of intracellular calcium ion stores.

A change in cytoplasmic calcium ion levels caused by release of calcium ions from intracellular stores is used to determine G-protein-coupled receptor function. This is another type of indirect assay. Among G-protein-coupled receptors are muscarinic acetylcholine receptors (mAChR), adrenergic receptors, sigma receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. Another type of indirect assay involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm.

Furthermore, there are cyclic nucleotide-gated ion channels, e.g., rod photoreceptor cell channels and olfactory neuron channels [see, Altenhofen, W. et al. (1991) *Proc. Natl. Acad. Sci U.S.A.* 88:9868–9872 and Dhallan et al. (1990) Nature 347:184–187] that are permeable to cations upon activation by binding of cAMP or cGMP. A change in cytoplasmic ion levels caused by a change in the amount of cyclic nucleotide activation of photo-receptor or olfactory neuron channels is used to determine function of receptors that cause a change in cAMP or cGMP levels when activated. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cell for this type of assay can be made by co-transfection of a host cell with DNA encoding a cyclic nucleotide-gated ion channel and a DNA encoding a receptor (e.g., certain metabotropic glutamate receptors, muscarinic acetylcholine receptors, dopamine receptors, serotonin receptors and the like, which, when activated, causes a change in cyclic nucleotide levels in the cytoplasm.

Any cell expressing a receptor protein which is capable, upon activation, of directly increasing the intracellular concentration of calcium, such as by opening gated calcium channels, or indirectly affecting the concentration of intracellular calcium as by causing initiation of a reaction which utilizes $Ca^{2+}$ as a second messenger (e.g., G-protein-coupled receptors), may form the basis of an assay. Cells endogenously expressing such receptors or ion channels and cells which may be transfected with a suitable vector encoding one or more such cell surface proteins are known to those of skill in the art or may be identified by those of skill in the art. Although essentially any cell which expresses endogenous ion channel and/or receptor activity may be used, it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells [see, Chasin (1986) Cell. Molec. Genet. 12:555] human embryonic kidney (HEK) cells (ATCC No. CRL1573), Chinese hamster ovary (CHO) cells (ATCC Nos. CRL9618, CCL61, CRL9096), PC12 cells (ATCC No. CRL1721) and COS-7 cells (ATCC No. CRL1651). Preferred cells for heterologous cell surface protein expression are those that can be readily and efficiently transfected. Preferred cells include HEK 293 cells, such as those described in U.S. Pat. No. 5,024,939.

Any compound which is known to activate ion channels or receptors of interest may be used to initiate an assay. Choosing an appropriate ion channel- or receptor-activating reagent depending on the ion channel or receptor of interest is within the skill of the art. Direct depolarization of the cell membrane to determine calcium channel activity may be accomplished by adding a potassium salt solution having a concentration of potassium ions such that the final concentration of potassium ions in the cell-containing well is in the range of about 50–150 mM (e.g., 50 mM KCl). With respect to ligand-gated receptors and ligand-gated ion channels, ligands are known which have affinity for and activate such receptors. For example, nicotinic acetylcoholine receptors are known to be activated by nicotine or acetylcholine; similarly, muscarinic and acetylcholine receptors may be activated by addition of muscarine or carbamylcholine.

Agonist assays may be carried out on cells known to possess ion channels and/or receptors to determine what effect, if any, a compound has on activation or potentiation of ion channels or receptors of interest. Agonist assays also may be carried out using a reagent known to possess ion channel- or receptor-activating capacity to determine whether a cell expresses the respective functional ion channel or receptor of interest.

Contacting a functional receptor or ion channel with agonist typically activates a transient reaction; and prolonged exposure to an agonist may desensitize the receptor or ion channel to subsequent activation. Thus, in general, assays for determining ion channel or receptor function should be initiated by addition of agonist (i.e., in a reagent solution used to initiate the reaction). The potency of a compound having agonist activity is determined by the detected change in some observable in the cells (typically an increase, although activation of certain receptors causes a decrease) as compared to the level of the observable in either the same cell, or substantially identical cell, which is treated substantially identically except that reagent lacking the agonist (i.e., control) is added to the well. Where an agonist assay is performed to test whether or not a cell expresses the functional receptor or ion channel of interest, known agonist is added to test-cell-containing wells and to wells containing control cells (substantially identical cell that lacks the specific receptors or ion channels) and the levels of observable are compared. Depending on the assay, cells lacking the ion channel and/or receptor of interest should exhibit substantially no increase in observable in response to the known agonist. A substantially identical cell may be derived from the same cells from which recombinant cells are prepared but which have not been modified by introduction of heterologous DNA. Alternatively, it may be a cell in which the specific receptors or ion channels are removed. Any statistically or otherwise significant difference in the level of observable indicates that the test compound has in some manner altered the activity of the specific receptor or ion channel or that the test cell possesses the specific functional receptor or ion channel.

In an example of drug screening assays for identifying compounds which have the ability to modulate ion channels or receptors of interest, individual wells (or duplicate wells, etc.) contain a distinct cell type, or distinct recombinant cell line expressing a homogeneous population of a receptor or ion channel of interest, so that the compound having unidentified activity may be screened to determine whether it possesses modulatory activity with respect to one or more of a variety of functional ion channels or receptors. It is also contemplated that each of the individual wells may contain the same cell type so that multiple compounds (obtained from different reagent sources in the apparatus or contained within different wells) can be screened and compared for modulating activity with respect to one particular receptor or ion channel type.

Antagonist assays, including drug screening assays, may be carried out by incubating cells having functional ion channels and/or receptors in the presence and absence of one or more compounds, added to the solution bathing the cells in the respective wells of the microtiter plate for an amount of time sufficient (to the extent that the compound has affinity for the ion channel and/or receptor of interest) for the compound(s) to bind to the receptors and/or ion channels, then activating the ion channels or receptors by addition of known agonist, and measuring the level of observable in the cells as compared to the level of observable in either the same cell, or substantially identical cell, in the absence of the putative antagonist.

The assays are thus useful for rapidly screening compounds to identify those that modulate any receptor or ion channel in a cell. In particular, assays can be used to test functional ligand-receptor or ligand-ion channel interactions for cell receptors including ligand-gated ion channels, voltage-gated ion channels, G-protein-coupled receptors and growth factor receptors.

Those of ordinary skill in the art will recognize that assays may encompass measuring a detectable change of a solution as a consequence of a cellular event which allows a compound, capable of differential characteristics, to change its characteristics in response to the cellular event. By selecting a particular compound which is capable of differential characteristics upon the occurrence of a cellular event, various assays may be performed. For example, assays for determining the capacity of a compound to induce cell injury or cell death may be carried out by loading the cells with a pH-sensitive fluorescent indicator such as BCECF (Molecular Probes, Inc., Eugene, Oreg. 97402, Catalog #B1150) and measuring cell injury or cell death as a function of changing fluorescence over time.

In a further example of useful assays, the function of receptors whose activation results in a change in the cyclic nucleotide levels of the cytoplasm may be directly determined in assays of cells that express such receptors and that have been injected with a fluorescent compound that changes fluorescence upon binding cAMP. The fluorescent compound comprises cAMP-dependent-protein kinase in which the catalytic and regulatory subunits are each labelled with a different fluorescent-dye [Adams et al. (1991) Nature 349:694–697]. When cAMP binds to the regulatory subunits, the fluorescence emission spectrum changes; this change can be used as an indication of a change in cAMP concentration.

The function of certain neurotransmitter transporters which are present at the synaptic cleft at the junction between two neurons may be determined by the development of fluorescence in the cytoplasm of such neurons when conjugates of an amine acid and fluorescent indicator (wherein the fluorescent indicator of the conjugate is an acetoxymethyl ester derivative e.g., 5-(aminoacetamido) fluorescein; Molecular Probes, Catalog #A1363) are transported by the neurotransmitter transporter into the cytoplasm of the cell where the ester group is cleaved by esterase activity and the conjugate becomes fluorescent.

In practicing an assay of this type, a reporter gene construct is inserted into an eukaryotic cell to produce a recombinant cell which has present on its surface a cell surface protein of a specific type. The cell surface receptor may be endogenously expressed or it may be expressed from a heterologous gene that has been introduced into the cell. Methods for introducing heterologous DNA into eukaryotic cells are-well known in the art and any such method may be used. In addition, DNA encoding various cell surface proteins is known to those of skill in the art or it may be cloned by any method known to those of skill in the art.

The recombinant cell is contacted with a test compound and the level of reporter gene expression is measured. The contacting may be effected in any vehicle and the testing may be by any means using any protocols, such as serial dilution, for assessing specific molecular interactions known to those of skill in the art. After contacting the recombinant cell for a sufficient time to effect any interactions, the level of gene expression is measured. The amount of time to effect such interactions may be empirically determined, such as by running a time course and measuring the level of transcription as a function of time. The amount of transcription may be measured using any method known to those of skill in the art to be suitable. For example, specific mRNA expression may be detected using Northern blots or specific protein product may be identified by a characteristic stain. The amount of transcription is then compared to the amount of transcription in either the same cell in the absence of the test compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription if the transcription is induced, the test compound is then assayed for its ability to inhibit, block or otherwise affect the activity of the agonist.

The transcription based assay is useful for identifying compounds that interact with any cell surface protein whose activity ultimately alters gene expression. In particular, the assays can be used to test functional ligand-receptor or ligand-ion channel interactions for a number of categories of cell surface-localized receptors, including: ligand-gated ion channels and voltage-gated ion channels, and G protein-coupled receptors.

Any transfectable cell that can express the desired cell surface protein in a manner such the protein functions to intracellularly transduce an extracellular signal may be used. The cells may be selected such that they endogenously express the cell surface protein or may be genetically engineered to do so. Many such cells are known to those of skill in the art. Such cells include, but are not limited to Ltk<–> cells, PC12 cells and COS-7 cells.

The preparation of cells which express a receptor or ion channel and a reporter gene expression construct, and which are useful for testing compounds to assess their activities, is exemplified in the Examples provided herewith by reference to mammalian Ltk<–>and COS-7 cell lines, which express the Type I human muscarinic (HMI) receptor and which are transformed with either a c-fos promoter-CAT reporter gene expression construct or a c-fos promoter-luciferase reporter gene expression construct.

Any cell surface protein that is known to those of skill in the art or that may be identified by those of skill in the art may used in the assay. The cell surface protein may endogenously expressed on the selected cell or it may be expressed from cloned DNA. Exemplary cell surface proteins include, but are not limited to, cell surface receptors and ion channels. Cell surface receptors include, but are not limited to, muscarinic receptors (e.g., human M2 (GenBank accession #M16404); rat M3 (GenBank accession #M16407); human M4 (GenBank accession #M16405); human M5 (Boner et al. (1988) Neuron 1:403410); and the like); neuronal nicotinic acetylcholine receptors (e.g., the alpha 2, alpha 3 and beta 2 subtypes disclosed in U.S. Ser. No. 504,455 (filed Apr. 3, 1990), hereby expressly incorporated by reference herein in its entirety); the rat alpha 2 subunit (Wada et al. (1988) Science 240:330–334); the rat alpha 3 subunit (Boulter et al. (1986) Nature 319:368–374); the rat alpha 4 subunit (Goldman et al. (1987) cell 48:965–973); the rat alpha 5 subunit (Boulter et al. (1990) J. Biol. Chem. 265:4472–4482); the rat beta 2 subunit (Deneris et al. (1988) Neuron 1:45–54); the rat beta 3 subunit (Deneris et al. (1989) J. Biol. Chem. 264: 6268–6272); the rat beta 4 subunit (Duvoisin et al. (1989) Neuron 3:487–496); combinations of the rat alpha subunits, beta subunits and alpha and beta subunits; GABA receptors (e.g., the bovine alpha 1 and beta 1 subunits (Schofield et al. (1987) Nature 328:221–227); the bovine alpha 2 and alpha 3 subunits (Levitan et al. (1988) Nature 335:76–79); the gamma-subunit (Pritchett et al. (1989) Nature 338:582–585); the beta 2 and beta 3 subunits (Ymer et alo (1989) EMBO J. 8:1665–1670); the delta subunit (Shivers, B. D. (1989) Neuron 3:327–337); and the like); glutamate receptors (e.g., receptor isolated from rat brain (Hollmann et al. (1989) Nature 342:643–648); and the like); adrenergic receptors (e.g., human beta 1 (Frielle et al. (1987) Proc. Natl. Acad. Sci. 84.:7920–7924); human alpha 2 (Kobilka et al. (1987) Science 238:650–656); hamster beta 2 (Dixon et al. (1986) Nature 321:75–79); and the like); dopaminc receptors (e.g., human D2 (Stormann et al. (1990) Molec. Pharm.37:1–6); rat (Bunzow et al. (1988) Nature 336:783–787); and the like); NGF receptors (e.g., human NGF receptors (Johnson et al. (1986) Cell 47:545–554); and the like); serotonin receptors (e.g., human 5HT1a (Kobilka et al. (1987) Nature 329:75–79); rat 5HT2 (Julius et al. (1990) PNAS 87:928–932); rat 5HT1c (Julius et al. (1988) Science 241:558–564); and the like).

Reporter gene constructs are prepared by operatively linking a reporter gene with at least one transcriptional regulatory element. If only one transcriptional regulatory element is included it must be a regulatable promoter, At least one of the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101).

Transcriptional control elements include, but are not limited to, promoters, enhancers, and repressor and activator binding sites, Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.*

14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to explott the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811–5814; Valerio et al. (1991) Anal Biochem 197:168–177; Bray et al. (1991) Tetrahedron Lett 32:6163–6166).

C) Divide-Couple-Recombine

In yet another embodiment, a variegated library of compounds can be provided on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271–280; Fodor, S. P. A. (1991) Science 251:767; Pirrung et al. (1992) U.S. Pat. No. 5,143,854; Jacobs et al. (1994) Trends Biotechnol 12:19–26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529–2531), orthogonality in synthesis is achieved by employing acid-labile protection for the coding strand and base-labile protection for the compound strand.

In an alternative approach (Nikolaiev et al. (1993) Pept Res 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention now being generally described, it will be more readily understood by reference to the following examples, which are included merely for purposes of illustration of certain aspects and embodiments of the present invention, and are not intended to limit the invention.

EXAMPLE 1

Preparation of 3-Hydroxymethyl-piperidine-1-carboxylic acid tert-butyl ester

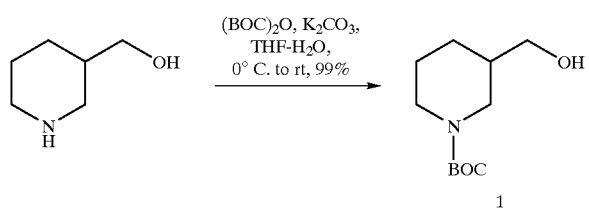

To a mixture of piperidin-3-yl-methanol (11.1 g, 96.37 mmol), $K_2CO_3$ (22.1 g, 160.0 mmol) in THF—$H_2O$ (50 mL-50 mL) at 0° C. was added $(BOC)_2O$ (23.2 ML, 101.18 mmol). The mixture was stirred overnight. The two layers were separated. Aqueous layer was extracted with EtOAc (2×50 mL). The combined organic solution was concentrated under vacuum. The residue was dissolved in EtOAc (100 mL), washed with sat. $NaHCO_3$, brine, 5% HCl and brine, and dried over $Na_2SO_4$. After filtration, the filtrate was evaporated under vacuum to give 1 as a colorless liquid (20.57 g, 99%). $^1$H-NMR (300 MHz, $CDCl_3$) δ 3.8 (broad, 2H), 3.41 (t, 2H) 3.00–2.70 (broad, 3H), 1.8–1.55 (broad, 3H), 1.4 (s, 9H), 1.2 (broad, 2H) ppm; $^{13}$C-NMR (75 MHz, $CDCl_3$) δ 155.43, 79.71, 64.63, 46.46, 45.30, 38.38, 28.64, 27.59, 24.30 ppm; IR (neat) 3440 (broad), 2976, 2931, 2857, 16921426, 1366, 1267, 1176, 1076 cm$^{-1}$.

EXAMPLE 2

Preparation of 3-Formyl-piperidine-1-carboxylic acid tert-butyl ester

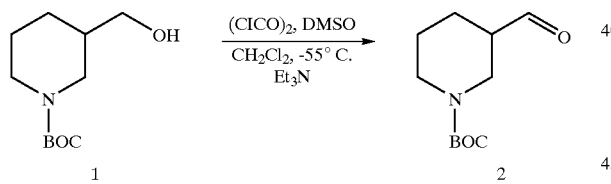

To a mixture of oxalyl chloride (6.5 mL, 65 mmol) in $CH_2Cl_2$ (1.60 mL) at –55° C. was added a solution of DMSO (11 mL) in $CH_2Cl_2$ (30 mL) in about 20 min. After addition, the mixture was stirred about 5 min at –55° C. Then, a solution of alcohol 1 (13.77 g, 63.9 mmol) in $CH_2Cl_2$ (160 mL) was added dropwise in 30 min. After addition, the mixture was stirred for 30 min followed by the addition of $Et_3N$ (44.8 mL). The mixture was stirred for 20 min and then allowed to warm up to room temperature. $H_2O$ (160 mL) was added. The two layers were separated. Aqueous layer was extracted with $CH_2Cl_2$. The combined organic solution was dried with $Na_2SO_4$, filtered and evaporated to afford 2 as a light yellow liquid (100% yield). $^1$H-NMR (300 MHz, $CDCl_3$)δ 9.7 (s, 1H), 3.95 (m, 1H), 3.70 (m, 1H), 3.30 (dd, 1H), 3.10 (m, 1H), 2.45 (m, 1H), 1.95 (m, 1H), 1.70 (m, 2H), 1.5 (s, 9H), 1.51 (m, 1H) ppm; $^{13}$C-NMR (75 MHz, $CDCl_3$) δ 202.33, 154.51, 79.54, 47.90, 43.61, 28.33, 27.31, 24.14, 23.74 ppm; IR (neat) 2936, 1724, 1692, 1402, 1365, 1266, 1150 cm$^{-1}$.

EXAMPLE 3

Preparation of 3-Phenylaminomethyl-piperidine-1-carboxylic acid tert-butyl Eester

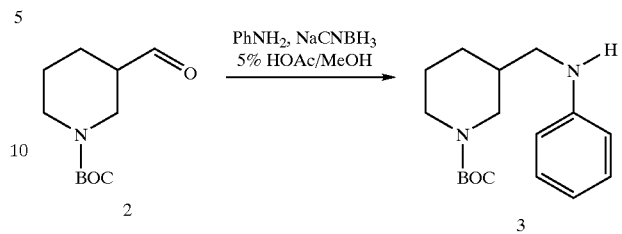

To a solution of aldehyde 2 (9.21 g, 43.23 mmol) in 5% HOAc in MeOH (100 mL) was added aniline (4.7 mL). The mixture was stirred at 0° C. for 10 min and $NaCNBH_3$ (5.8 g, 92.3 mmol) was added slowly. The mixture was stirred at room temperature for 48 hrs. The reaction was quenched by addition of aq. $NaHCO_3$ (50 mL), extracted with EtOAc (2×50 mL). The combined organic solutions were dried with $Na_2SO_4$, filtered and evaporated. The crude product was purified by silica gel chromatography (5–10% EtOAc in hexane as eluent) to give 3 as a light yellow liquid (10.0 g, 80% yield). $^1$H-NMR (300 MHz, $CDCl_3$) δ 7.20 (t, 2H), 6.70 (m, 2H), 6.60 (d, 1H), 3.90 (m, 2H), 3.80 (m, 2H), 3.00 (m, 3H), 3.75 (m, 1H), 1.84 (m, 2H), 1.70 (m, 1H), 1.60 (s, 9 h), 0.9 (m, 1H) ppm; $^{13}$C-NMR (75 MHz, $CDCl_3$) δ 155.13, 148.60, 129.46, 117.27, 112.92, 79.57, 53.82, 47.98, 46.91, 45.12, 35.67, 28.99, 28.71, 28.02, 24.56 ppm.

EXAMPLE 4

Preparation of 3-[(methanesulfonyl-phenyl-amino)-methyl]-piperidine-1-carboxylic acid tert-butyl ester

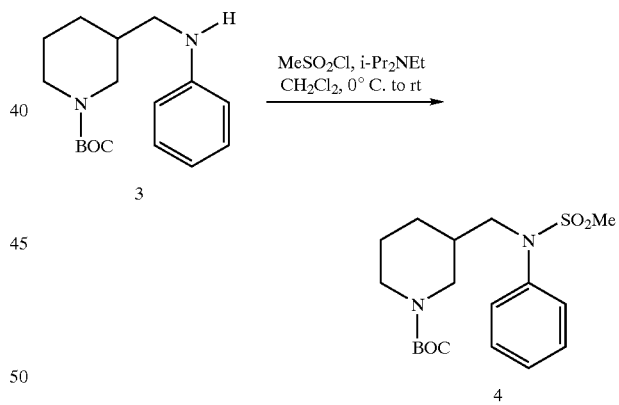

To a solution of 3-Phenylaminomethyl-piperidine-1-carboxylic acid tert-butyl ester 3 (8.6 g, 29.66 mmol), i-$Pr_2$NEt (10 mL, 59.32 mmol) in $CH_2Cl_2$ (50 mL) at 0° C. was added methanesulfonyl chloride (3.0 mL, 38.55 mmol). The mixture was stirred for 3 hrs at room temperature. Aqueous $NaHCO_3$ (40 mL) was added. The two layers were separated. Aqueous layer was extracted with $CH_2Cl_2$ (2×40 mL). The combined organic solution was dried with $Na_2SO_4$, filtered and evaporated. The crude product was purified by silica gel chromatography (20% EtOAc in hexane, then 100% $CH_2Cl_2$) to afford 4 as a white solid (9.58 g). $^1$H-NMR (300 MHz, $CDCl_3$) δ 7.40 (m, 5H), 4.00 (m, 2H), 3.60 (m, 2H), 2.90 (s, 3H), 2.75 (m, 2H), 1.83–1.20 (m, 5H), 1.48 (s, 9H) ppm; $^{13}$C-NMR (75 MHz, $CDCl_3$) δ 154.85, 139.44, 129.80, 128.61, 128.46, 79.60, 53.64, 47.86, 44.19, 36.86, 34.80, 28.66, 24.37 ppm; IR (neat) 3003, 2975, 2931, 2854, 1692, 1596, 1495, 1427, 1343, 1266, 1246, 1154, 1110, 1069 cm$^{-1}$.

EXAMPLE 5

Preparation of N-phenyl-N-piperidin-3-ylmethyl-methanesulfonamide

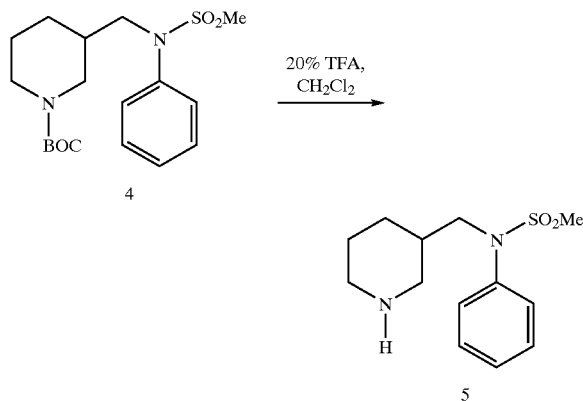

To a solution of N-(1-Boc-piperidin-3-ylmethyl)-N-phenyl methylsulfonamide 4 (1.11 g, 3.12 mmol) in CH$_2$C$_2$ (5 mL) at 0° C. was added TFA (5 mL). After stirring for 1 hr, solvent and excess TFA was removed by evaporation. The residue was dissolved in 20 mL of 5% HCl, washed with EtOAc (2×30 mL). The organic solution was discarded. The aqueous solution was neutralized with K$_2$CO$_3$, extracted with EtOAc (2×30 mL). The combined extracts were dried with Na$_2$SO$_4$, filtered and evaporated to afford 5 as a white solid. $^1$H-NMR (300 MHz, CDCl$_3$) δ 7.30 (m, 5H), 5.20 (broad s, 1H), 3.60 (m, 2H), 3.20 (d, 1H), 3.05 (d, 1H), 2.81 (s, 3H), 2.60 (t, 1H), 2.40 (t, 1H), 1.78 (m, 3H), 1.50 (m, 1H), 1.18 (m, 1H) ppm; $^3$C-NMR (75 MHz, CDCl$_3$) d 139.51, 129.89, 128.63, 128.53, 54.18, 48.79, 45.73, 36.85, 34.46, 27.74, 23.95 ppm; IR (neat) 3059, 3019, 2931, 2850, 2810, 2738, 1600, 1495, 1455, 1266, 1158, 1069, 965, 872 cm$^{-1}$; LRMS [calculated for C$_{13}$H$_{21}$N$_2$O$_2$S, (M+1)$^+$] 269, found 269.

EXAMPLE 6

Preparation of N-(1-phenethyl-pieridin-3-ylmethyl)-N-phenyl-methanesulfonamide

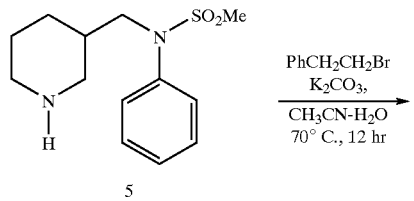

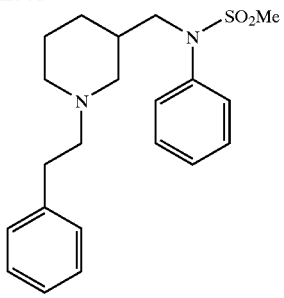

The mixture of amine 5 (750 mg, 2.79 mmol), (2-bromoethyl)-benzene (0.44 mL), CH$_3$CN (4 mL), H$_2$O (4 mL), K$_2$CO$_3$ (0.77 g, 5.6 mmol) was stirred at 70° C. for 12 hrs. After cool down to room temperature, the organic layer was separated. Aqueous layer was extracted with EtOAc (2×10 mL). The combined organic solution was dried with Na$_2$SO$_4$, filtered and evaporated. The crude product was purified by flash silica gel chromatography (20% EtOAc in hexane) to give 6 as a colorless oil (968 mg, 93%). $^1$H-NMR (300 MHz, CDCl$_3$) δ 7.3–7.20 (m, 10H), 3.62 (d, 2H), 2.95 (m, 1H), 2.90–2.75 (m, 6H), 2.60 (m, 2H), 2.10 (m, 1H), 1.90–1.80 (m, 4H), 1.50 (m, 1H), 1.10 (m, 1H) ppm; $^{13}$C-NMR (75 MHz, CDCl$_3$) δ 140.75, 139.58, 129.84, 129.01, 128.64, 128.67, 128.37, 126.26, 61.24, 57.72, 54.42, 36.74, 35.06, 33.87, 28.48, 24.92 ppm; LRMS [calculated for C$_{21}$H$_{29}$N$_2$O$_2$S, (M+1)$^+$]373, found 373.

EXAMPLE 7

Preparation of (R)-3-Phenylcarbamoyl-piperidine-carboxylic acid tert-butyl ester

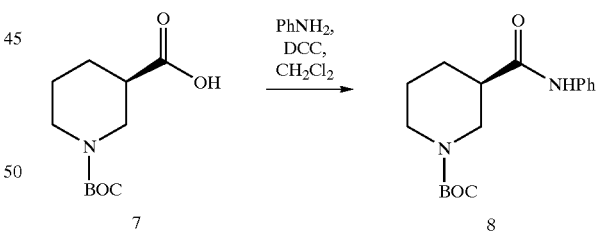

To a solution of (R)-piperidine-1,3-dicarboxylic acid-1-tert-butyl ester 7 (2.03 g, 8.86 mmol), aniline (80.89 mL, 9.75 mmol) in CH$_2$Cl$_2$ (20 mL) at 0° C. was added DCC (2.19 g, 10.63 mmol) in several portion. The mixture was stirred at room temperature for 3 hrs. The white precipitate was removed by filtration through Celite. The filtrate was washed with 5% HCl, sat. NaHCO$_3$ and then dried over Na$_2$SO$_4$, filtered and evaporated. The residue was dried by azotropic evaporation with benzene to give 8 as a white solid. LRMS [calculated for C$_{17}$H$_{25}$N$_2$O$_4$ (M+1)$^+$] 304, found 304.

EXAMPLE 8

Preparation of 3-Phenylaminomethyl-piperidine-1-carboxylic acid tert-butyl ester

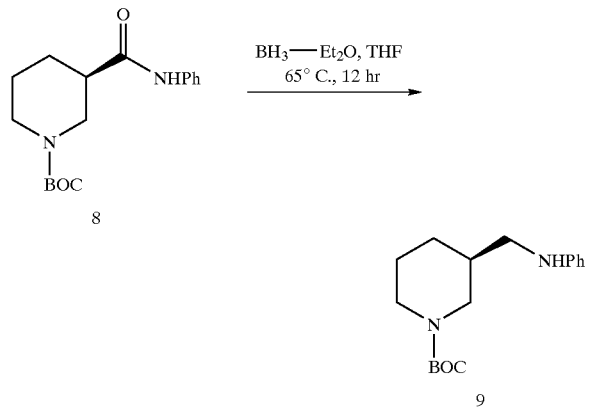

To a solution of (R)-3-Phenylcarbamoyl-piperidine-carboxylic acid tert-butyl ester 8 in THF (22 mL) was added BH$_3$-ether (1.0 M, 20 mL) at 0° C. The mixture was stirred for 10 min and then refluxed under N$_2$ overnight. Aqueous NaHCO$_3$ (30 mL) was added to quench the reaction. The mixture was extracted with EtOAc (3×30 mL). The combined organic solution was dried with Na$_2$SO$_4$, filtered and evaporated. Chromatography (silica gel, 10–20% EtOAc in hexane) afforded 9 as a colorless oil. LRMS [calculate for C$_{17}$H$_{27}$N$_2$O$_2$, (M+1)$^+$] 291, found 291.

EXAMPLE 9

Preparation of (R)-N-(1-phenethyl-pieridin-3-ylmethyl)-N-phenyl-methanesulfonamide

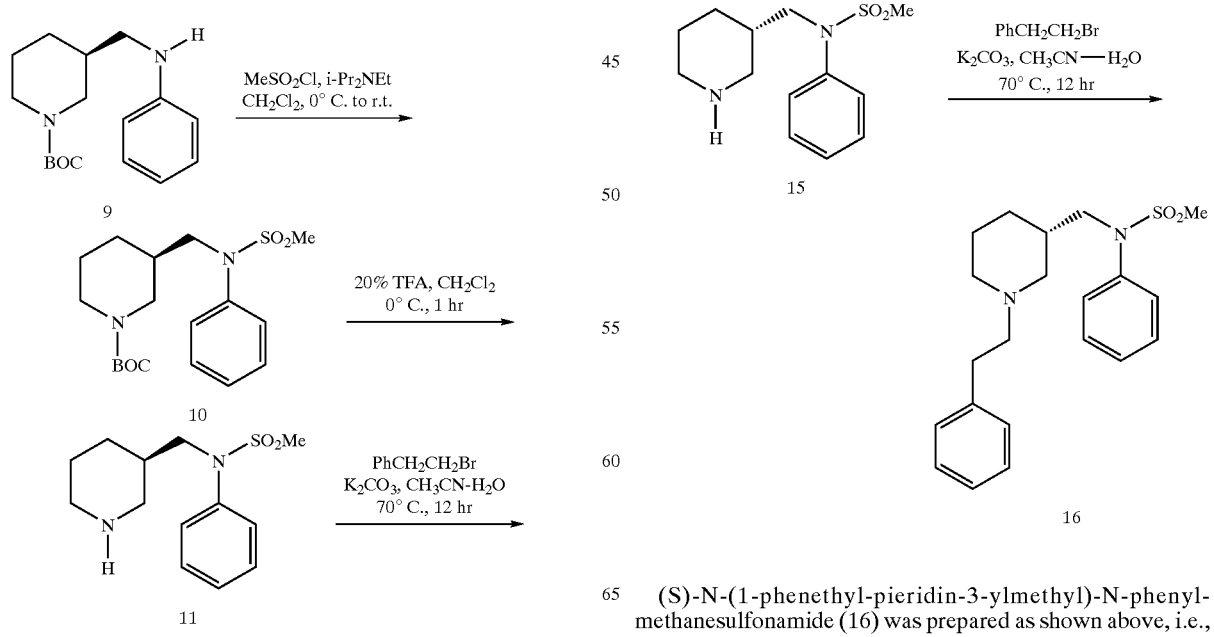

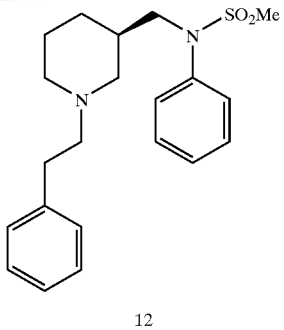

(R)-N-(1-phenethyl-pieridin-3-ylmethyl)-N-phenyl-methanesulfonamide (12) was prepared as shown above, using the same experimental procedures as described for the preparation of its racemic counterpart, 6. HPLC: Rt==16.57 min (ChiralPak AD column, 10% i-PrOH, 0.1% Et$_2$NH in hexane, 1 mL/min, 254 nm).

EXAMPLE 10

Preparation of (S)-N-(1-phenethyl-pieridin-3-ylmethyl)-N-phenyl-methanesulfonamide (S)-N-(1-phenethyl-pieridin-3-ylmethyl)-N-phenyl-methanesulfonamide (16) was prepared as shown above, i.e., in the same fashion used for 12. HPLC: Rt=13.92 min (ChiralPak AD column, 10% i-PrOH, 0.1% Et$_2$NH in hexane, 1 mL/min, 254 mm).

EXAMPLE 11

SEPARATION OF (R) AND (S)N-(1-PHENETHYL-PIERIDIN-3-YLMETHYL)-N—PHENYL-METHANESULFONAMIDE

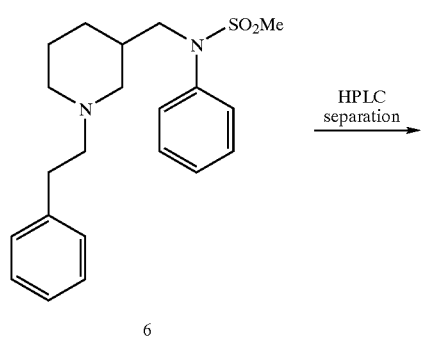

6

HPLC separation →

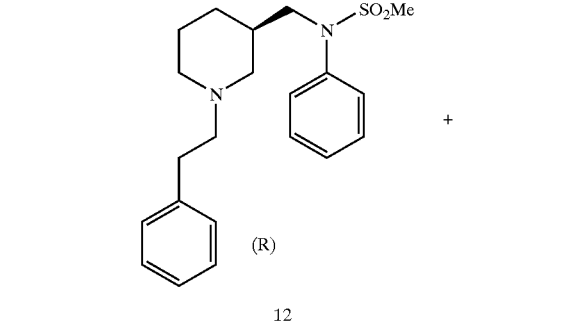

12 (R)

+

16 (S)

The two homogeneous enantiomers (12 and 16) were also obtained by chiral HPLC separation of the racemate 6 (ChiralPak AD column, 10% i-PrOH, 0.1% Et$_2$NH in hexane, 4.7 mL/min, 254 nm): Rt$_1$=13.92 min (16), Rt$_2$=17.02 min (12).

EXAMPLE 12

Preparation of N-1-Carbobenzyloxy[3-R-(2'-anillino)carobxy)piperidine

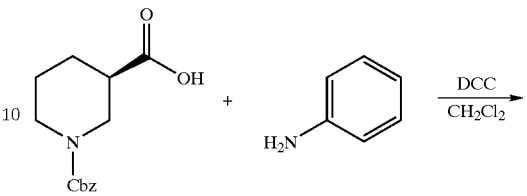

17

A solution of R-Cbz-nipecotic acid (0.038 mol, 10.0 g) and aniline (4.0 equiv, 0.15 mmol, 14 mL) in CH$_2$Cl$_2$ at 0° C. was treated with DCC (1.5 equiv, 0.057 mol, 12.0 g) under Ar. The reaction mixture was allowed to warm to 25° C. and stirred for 12 h. The reaction mixture was then filtered to remove the urea and the solvents were removed in vacuo. Chromatography (SiO$_2$, 2.5 cm×30.5 cm, 1:1 hexane-EtOAc) provided 17 (10.0 g, 12.8 g theoretical, 78%) as a white foam: R$_f$0.45 (SiO$_2$, 1:1 hexane-EtOAc); LRMS m/z 338 (M$^+$, C$_{20}$H$_{22}$N$_2$O$_3$, requires 338).

EXAMPLE 13

Preparation Of Piperidine-3-R-carboxilic acid phenylamide

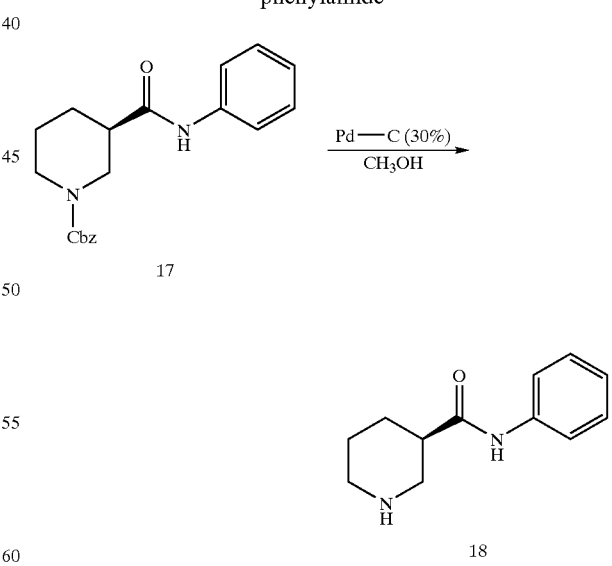

A solution of 17 (0.015 mol, 5.0 g) and Pd-C 30% (100 mg) in CH$_3$OH at 25° C. were added to a Paar hydrogenator low pressure reaction vessel. The mixture was reacted at 55 psi with vigorous shaking until hydrogen uptake subsided (2 h). The catalyst was filtered through a pad of Celite. The filtrate was concentrated in vacuo which provided 18 (3.0 g, 3.0 g theoretical, 99%) as a white foam: LRMS m/z 204 (M+, $C_{12}H_{16}N_2O$, requires 204).

EXAMPLE 14

Preparation of 1-[1-(4-Chloro-phenyl) cyclobutanecarbonyl]-piperidine-3-R-carboxylic acid phenylamide

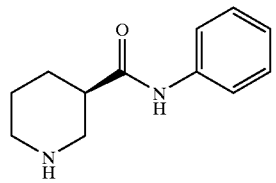

18

+

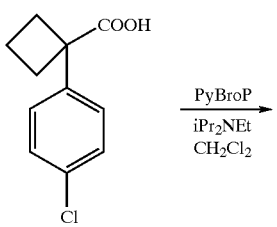

PyBroP
iPr$_2$NEt
CH$_2$Cl$_2$

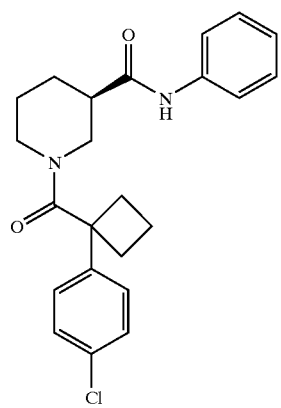

19

A solution of 18 (2.95 mmol, 603 mg), 1-(4-chlorophenyl)-1-cyclobutane carboxylic acid (1.5 equiv, 4.43 mmol, 932 mg) and iPr$_2$NEt (3.0 equiv, 8.85 mmol, 1.5 mL) in CH$_2$Cl$_2$ (10 mL) was treated with PyBroP (1.5 equiv, 4.43 mmol, 2.07 g) under Ar at 0° C. After warming to 25° C. and stirring for 12 h, the reaction mixture was quenched with 10% aqueous HCl and extracted with EtOAc (3×25 mL). The organic layer was then washed with NaHCO$_{3(sat)}$ and dried with NaCl$_{(sat)}$ and MgSO$_{4(s)}$. Chromatography (SiO$_2$, 2.5 cm×30.5 cm, 2:1 hexane-EtOAc) provided 19 (0.851 g, 1.17 g theoretical, 73%) as a white foam: R$_f$ 0.17 (SiO$_2$, 2:1 hexane-EtOAc); LRMS m/z 396 (M+, $C_{23}H_{25}ClN_2O_2$, requires 396).

EXAMPLE 15

Preparation of {1-[1-(4-Chloro-phenyl)-cyclobutylmethyl]-piperidin-3-R-ylmethyl]-phenyl-amine

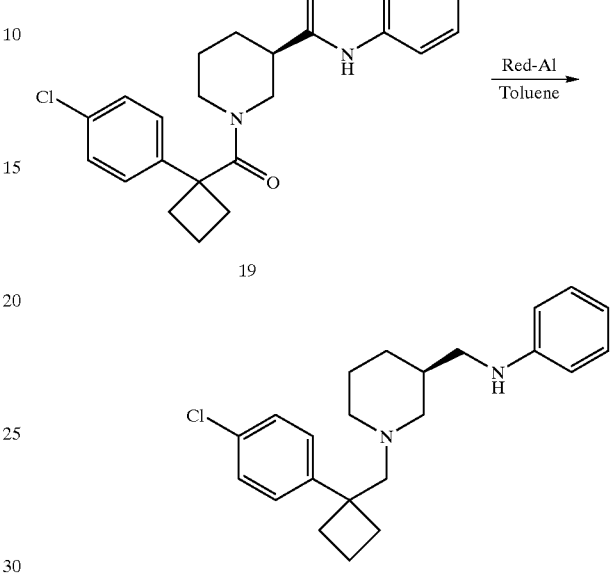

A solution of 19 (0.504 mmol, 200 mg) in toluene (2 mL) at 0° C. was treated with 3.0 M Red-Al (3.5 equiv, 1.76 mmol) under Ar. The reaction mixture stirred for 12 h and returned to 25° C. The reaction mixture was then cooled to 0° C., quenched with 10% aqueous NaOH and extracted with EtOAc (3×25 mL). The organics were dried with NaCl$_{(sat)}$ and Na$_2$SO$_{4(s)}$. The reaction mixture was purified by chromatography (PTLC, SiO$_2$, 20 cm×20 cm, 1 mm, 2:1 hexane-EtOAc) which provided 20 (170 mg, 186 mg theoretical, 91%) as a colorless oil: R$_f$ 0.61 (SiO$_2$, 2:1 hexane-EtOAc); LRMS m/z 368 (M+, $C_{23}H_{29}ClN_2$, requires 368).

EXAMPLE 16

Preparation of N-{1-[1-(4-Chloro-phenyl)-cyclobutylmethyl]-piperidin-3-R-ylmethyl}-N-phenyl-methanesulfon-amide

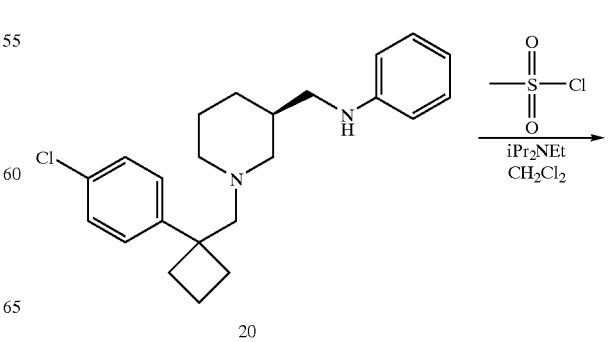

-continued

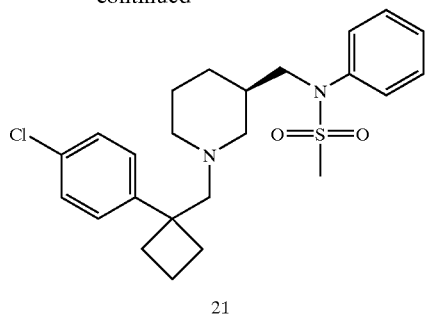

21

A solution of 20 (0.136 mmol, 50 mg) in CH$_2$Cl$_2$ (1 mL) at 0° C. was treated with methylsulfonyl chloride (1.2 equiv, 0.163 mmol, 36 μL) and diisopropylethylamine (1.5 equiv, 0.204 mmol, 36 μL) under Ar. After warming to 25° C. and stirring for 12 h, the reaction mixture was purified directly by chromatography (PTLC, SiO$_2$, 20 cm×20 cm, 1 mm, 2:1 hexane-EtOAc) which provided 21 (55 mg, 61 mg theoretical, 90%) as a colorless oil: R$_f$ 0.55 (SiO$_2$, 2:1 hexane-EtOAc); LRMS m/z 447 (M$^+$, C$_{24}$H$_{31}$ClN$_2$O$_2$S, requires 447).

EXAMPLE 17

Preparation of N-{1-[1-(4-chloro-phenyl)-cyclobutylmethyl]-piperidin-3-R-ylmethyl}-N-phenyl-sulfonylurea

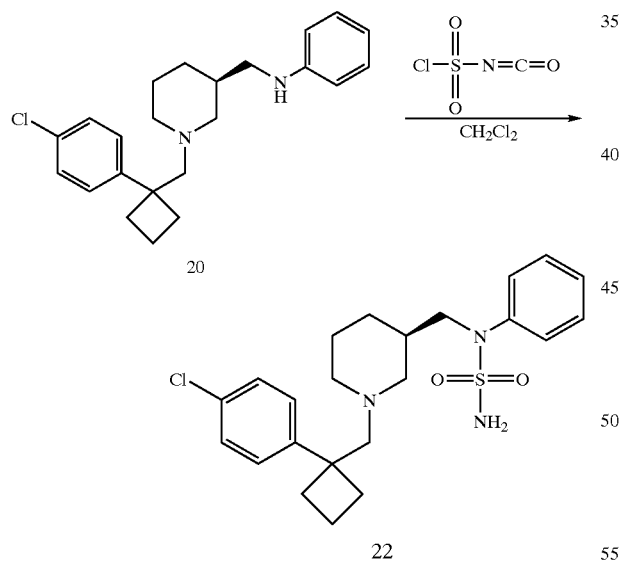

A solution of the 20 (0.320 mmol, 118 mg) in CH$_2$Cl$_2$ (1 mL) at 0° C. was treated with chlorosulfonyl isocyanate (1.2 equiv, 0.384 mmol, 33 μL) under Ar. After warming to 25° C. and stirring for 12 h, the reaction mixture was purified directly by chromatography (PTLC, SiO$_2$, 20 cm×20 cm, 1 mm, 1:1 hexane-EtOAc) which provided 22 (12 mg, 143 mg theoretical, 8%) as a colorless oil: R$_f$ 0.28 (SiO$_2$, 1:1 hexane-EtOAc); LRMS m/z 448 (M$^+$, C$_{23}$H$_{30}$ClN$_3$O$_2$S, requires 448).

EXAMPLE 18

Synthesis of N-{1-[2-(Chloro-phenyl)-2-oxo-ethyl]-piperidin-3ylmethyl}-N-phenyl-methanesulfonamide

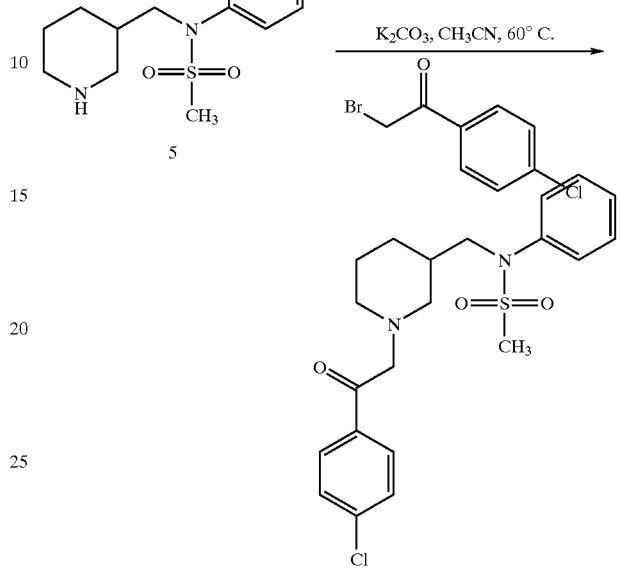

The mixture of amine 5 (0.25 g, 0.678 mmol), 2-bromo-1-(4-chloro-phenyl)-ethanone (0.237 g, 1.016 mmol), K$_2$CO$_3$ (0.281 g, 2.03 mmol), and CH$_3$CN (2 mL) was stirred at 60° C. for 12 h. After cool down to room temperature the reaction mixture was diluted with water. The aqueous layer was extracted with EtOAc (3×, 5 mL). Combined organic layers were dried over Na$_2$SO$_4$ and concentrated to yield a crude oil. Silica gel chromatography (100% hexane-100% EtOAc) afforded 23 (9.4 mg) as a clear oil. LRMS (calculated for C$_{21}$H$_{25}$ClN$_2$O$_3$S) 421, found 421.

EXAMPLE 19

Synthesis of N-{1-[2-(Chloro-phenyl)-2-hydroxy-ethyl]-piperidin-3ylmethyl}-N-phenyl-methanesulfonamide

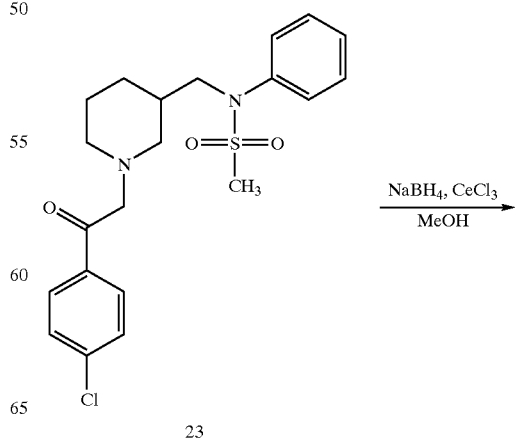

-continued

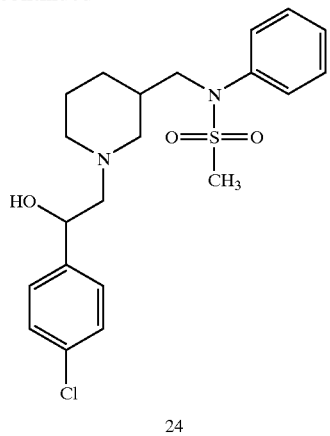

24

A mixture of ketone 23 (8.4 mg, 0.02 mmol), NaBH₄ (2.26 mg, 0.06 mmol), CeCl₃ (7.42 mg, 0.02 mmol) and MeOH (1 mL) was stirred at RT. After 12 h, the reaction was quenched with water. The aqueous layer was extracted with EtOAc (3×1 mL). Combined organic layers were dried over Na₂SO₄ and concentrated to yield a crude oil. Silica gel prep TLC (100% EtOAc) afforded 24 (1.4 mg) as an oil. LRMS: M+423.

EXAMPLE 20

Synthesis of of N-{1-[2-(chloro-phenyl)-cyclobutyl-2-oxo-ethyl]-piperidin-3ylmethyl}-N-phenyl-methanesulfonamide

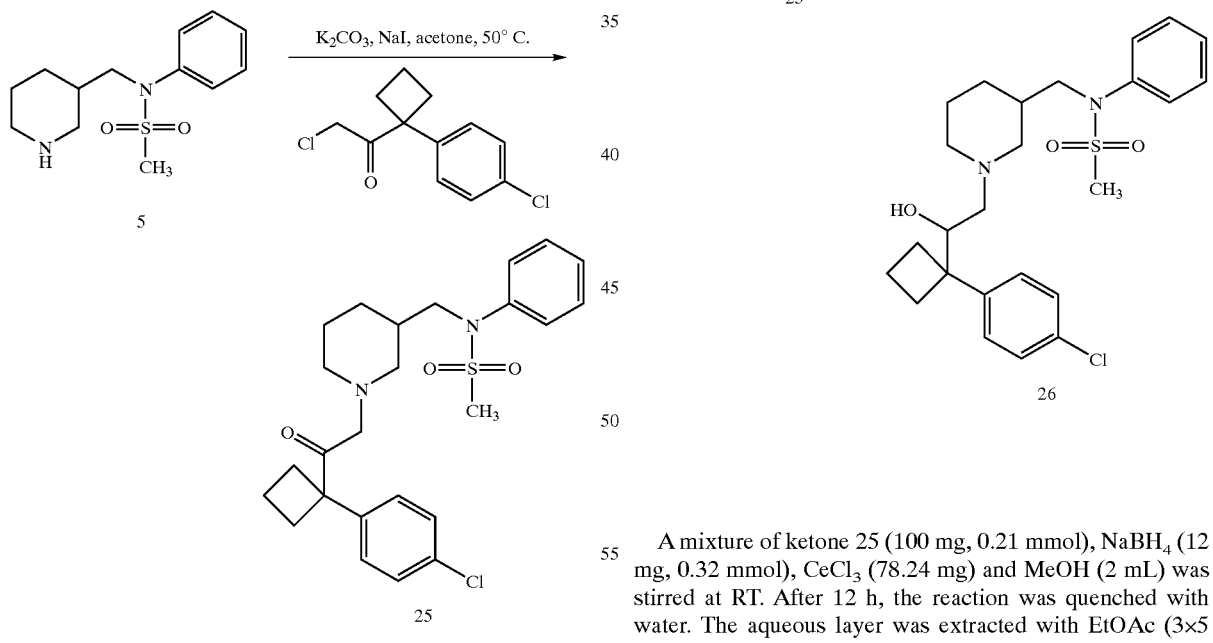

To a solution of 2-chloro-1-[1-(4-chloro-phenyl)-cyclobutyl]-ethanone (164 mg, 0.678 mmol) in acetone (1 mL) was added sodium iodide (102 mg, 0.678 mmol). After 5 min at room temperature, the mixture was added to a mixture of 5 (250 mg, 0.678 nmol) and K₂CO₃ (375 mg, 2.71 mmol) in acetone (1.5 mL). The resulting reaction mixture was heated to 50° C. After 12 h the reaction cooled down to RT and water was added. The aqueous layer was extracted with EtOAc (3×5 mL). Combined organic layers were dried over Na₂SO₄ and concentrated to yield a crude oil. Silica gel chromatography (4:1 hexane:EtOAc-1:1 hexane:EtOAc) afforded 25 (174.4 mg,) as an oil. LRMS: M+475. ¹H NMR (300 MHz, CDCl₃) δ 7.43–7.16 (9H, m), 3.52 (2H, d,J=6.23 Hz), 3.08 (2H, d,J=4.27 Hz), 2.85 (3H, s), 2.41–1.60 (15H, m).

EXAMPLE 21

Synthesis of N-{1-[2-(chloro-phenyl)-cyclobutyl-2-hydroxy-ethyl]-piperidin-3-ylmethyl}-N-phenyl-methanesulfonamide

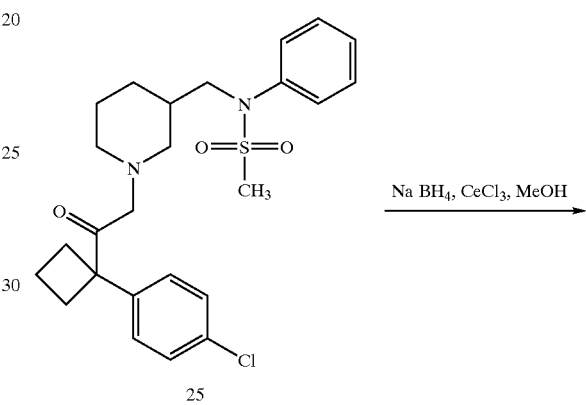

A mixture of ketone 25 (100 mg, 0.21 mmol), NaBH₄ (12 mg, 0.32 mmol), CeCl₃ (78.24 mg) and MeOH (2 mL) was stirred at RT. After 12 h, the reaction was quenched with water. The aqueous layer was extracted with EtOAc (3×5 mL). Combined organic layers were dried over Na₂SO₄ and concentrated to yield a crude oil. Silica gel prep TLC (3:100 2M NH₃ in EtOH: DCM) afforded 26 (35 mg,) as an oil. LRMS: M+477. ¹H NMR (300 MHz, CDCl₃) δ 7.44–7.11 (9H, m), 4.15 (1H, m), 3.89 (2H, m), 3.90 (2H, m), 2.87 (3H, s), 2.58–1.11 (15H, m). ¹³C-NMR (75 MHz, CDCl₃) δ 145.1, 139.7, 139.9, 131.8, 129.9, 128.9, 128.6, 128.1, 71.3, 59.8, 56.4, 54.1, 48.9, 36.8, 34.9, 31.1, 29.2, 27.8, 24.2, 16.3 ppm.

EXAMPLE 22

3-(2-PHENOXY-PHENYLCARBAMOYL)-PIPERIDINE-1-CARBOXYLIC ACID TERT-BUTYL ESTER

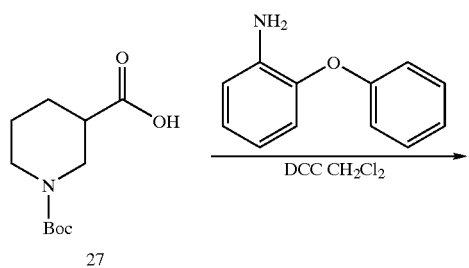

To a solution of 27 (0.3 g, 1.3 mmol) in dichloromethane (7 mL) were added 2-phenoxyaniline (0.259 g, 1.4 mmol) and DCC (0.289 g, 1.4 mmol). The mixture was stirred at room temperature overnight. The reaction mixture was passed through a filter paper to remove the solid urea formed during the reaction. The filtrate was poured into a separatory funnel and additional dicloromethane (20 mL) was added. The organic layer was sequentially washed with 5% HCl (30 mL) and brine (30 mL), dried over $Na_2SO_4$, filtered and evaporated. Finally, the crude product was purified by column chromatographic on silica gel (230–400 Mesh) using hexane/ethyl acetate (8:2) as eluent to afford 28 as an orange oil (0.211 g). LRMS [calculated for $(M+1)^+$:396] observed: 396.

EXAMPLE 23

3-[(2-PHENOXY-PHENYLAMINO)-METHYL]-PIPERIDINE-1-CARBOXYLIC ACID TERT-BUTYL ESTER

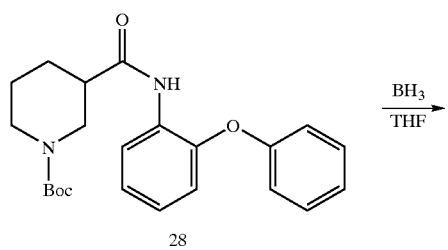

To a solution of 28 (0.211 g, 0.53 mmol) in tetrahydrofuran (2 mL) was added a 1.0 M solution of borane-tetrahydrofuran complex (1.6 mL, 1.6 mmol) at 0° C. The reaction mixture was heated at 75° C. overnight. The excess of borane was carefully quenched at 0° C. using a 5% HCl solution (3 mL). The mixture was brought to the basic range (12<pH<14) using a 10% NaOH solution (5 mL). Than the mixture was poured into a separatory funnel and ethyl acetate (15 mL) was used for the extraction. The organic layer was recovered, dried over $Na_2SO_4$, filtered and evaporated. Finally, the crude product was purified by column chromatography on silica gel (230–400 Mesh) using hexane/ethyl acetate (8:2) as eluent to afford 29 as an almost colorless oil (0.150 g). LRMS [calculated for $(M+1)^+$:383] observed: 383.

EXAMPLE 24

3-{[(Methanesulfonyl-(2-phenoxy-phenyl)-amino]-methyl}-piperidine-1-carboxylic acid tert-butyl ester

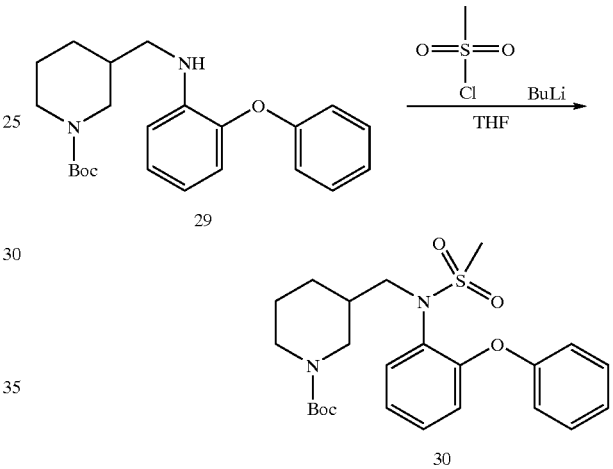

To a solution of 29 (0.15 g, 0.39 mmol) in tetrahydrofuran (0.5 mL) at −78° C. was added dropwise methanesulfonyl chloride (151 µl, 1.95 mmol) and a 1.6 M solution of butyl lithium (1.95 mL, 3.12 mmol). The reaction mixture was stirred at room temperature for two hours. The crude mixture was concentrated and than purified by preparative thin layer chromatography (TLC) using hexane/ethyl acetate (7:3) as eluent to afford 30 as a colorless oil (15 mg). LRMS [calculated for $(M+1)^+$:461] observed: 461.

EXAMPLE 25

N-(1-Phenethyl-piperidin-3-ylmethyl)-N-(2-phenoxy-phenyl)-methanesulfonamide

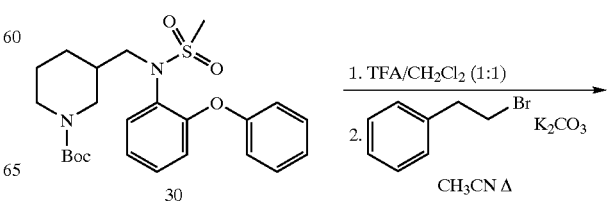

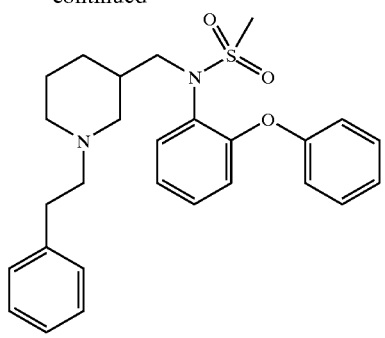

31

To a vial were added 30 (15 mg, 0.033 mmol) and a 1:1 solution of trifluoroacetic acid/dichloromethane (0.5 mL). The reaction mixture was stirred at room temperature for 30 minutes. Than the mixture was evaporated and dried under vacuum. Then, acetonitrile (200 μL), $K_2CO_3$ (13.5 mg, 0.098 mmol) and (2-Bromoethyl)benzene (9 μL, 0.065 mmol) were added and the reaction mixture stirred at 50° C. overnight. The mixture was poured into a separatory funnel and ethyl acetate (8 mL) was used for the extraction. The organic layer was sequentially washed with a 10% NaOH solution and brine, dried over $Na_2SO_4$, filtered and evaporated. Finally, the crude product was purified by preparative TLC using dichloromethane/methanol (95:5) to afford 31 as a slightly orange oil (10 mg). LRMS [calculated for $(M+1)^+$ :465] observed: 465.

EXAMPLE 26

3-{[Phenyl-(4-trifluoromethoxy-benzenesulfonyl-amino]-methyl}-piperidine-1-carboxylic acid tert-butyl ester

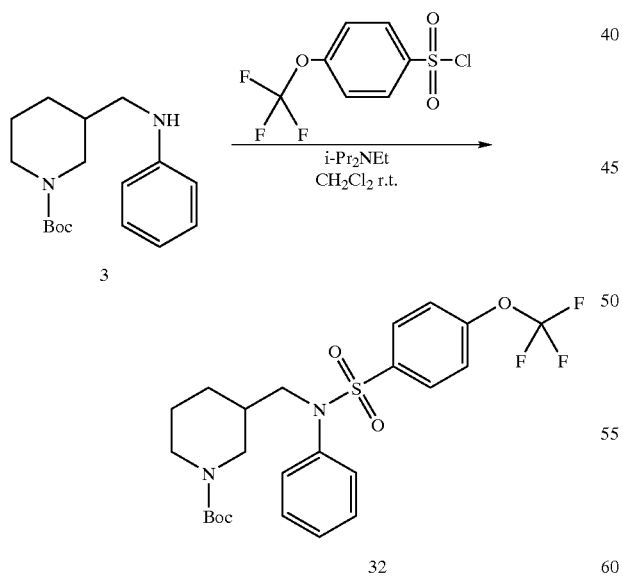

To a solution of 3 (0.4 g, 1.38 mmol) dissolved in dichloromethane (3 mL) were added at 0° C. N,N-Diisopropylethylamine (0.721 mL, 4.14 mmol) and 4-(Trifluoromethoxy)benzene sulfonyl chloride (0.468 mL, 2.76 mmol). The reaction mixture was stirred at room temperature overnight. The mixture was than poured into a separatory funnel and additional dichloromethane (15 mL) was added for the extraction. The organic layer was sequentially washed with a solution of 5% HCl, a solution of 10% NaOH and with brine, dried over $Na_2SO_4$, filtered and evaporated. Finally, the crude product was purified by column chromatographic on silica gel (230–400 Mesh) using hexane/ethyl acetate (8:2) as eluent to afford 32 as an almost colorless oil (0.65 g). LRMS [calculated for $(M+1)^+$ :516] observed: 516.

EXAMPLE 27

N-(1-Phenethyl-piperidin-3-ylmethyl)-N-phenyl-4-tri fluoromethoxy-benzenesulfonamide

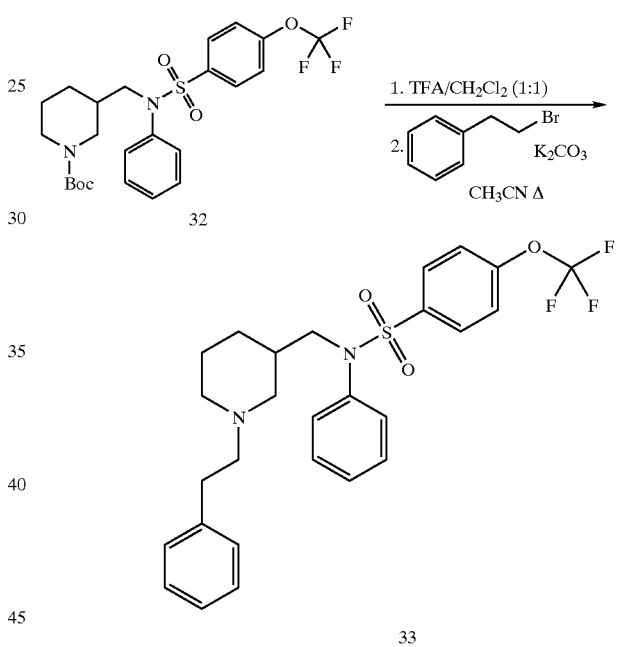

To a vial were added 32 (0.15 g, 0.29 mmol) and a 1:1 solution of trifluoroacetic acid/dichloromethane (1 mL). The reaction mixture was stirred at room temperature for 30 minutes. Then, the mixture was evaporated and dried under vacuum. Then, acetonitrile (0.55 ML), potassium carbonate (0.12 g, 0.87 mmol) and (2-bromoethyl)benzene (0.079 mL, 0.58 mmol) were added. The reaction mixture was stirred at 50° C. overnight. Then, the mixture was poured into a separatory funnel and ethyl acetate (10 mL) was used for the extraction. The organic layer was sequentially washed with a 10% NaOH solution and with brine, dried over $Na_2SO_4$, filtered and concentrated. Finally, the crude product was purified by preparative TLC using dichloromethane/methanol (95:5) as eluent to afford 33 as a colorless oil (0.107 g). LRMS [calculated for $(M+1)^+$:520) observed: 520.

EXAMPLE 28

3-{[(4-Bromo-benzenesulfonyl-phenyl-amino]-methyl}-piperidine-1-carboxylic acid tert-butyl ester

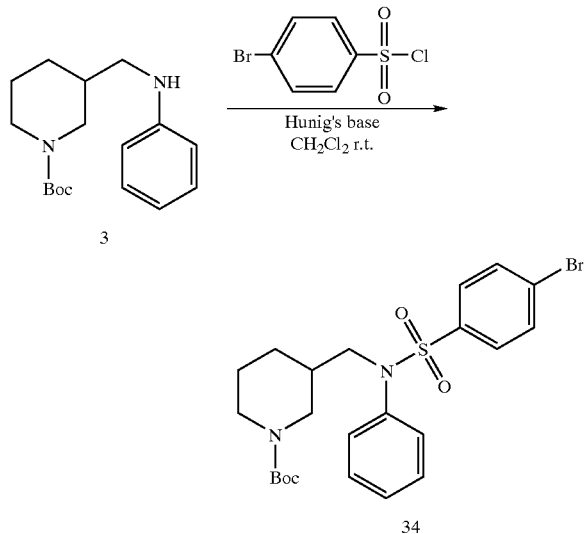

To a solution of 3 (0.4 g, 1.38 mmol) dissolved into dichloromethne (3 mL) were added at 0° C. N,N-Diisopropylethylamine (0.721 mL, 4.14 mmol) and 4-bromobenzenesulfonyl chloride 0.705 mg, 2.76 mmol). The reaction mixture was stirred at room temperature overnight. The mixture was then poured into a separatory funnel and additional dichloromethane (15 mL) was added for the extraction. The organic layer was sequentially washed with a solution of 5% HCl, a solution of 10% NaOH and with brine, dried over $Na_2SO_4$, filtered and evaporated. Finally, the crude product was purified by column chromatographic on silica gel (230∝400 Mesh) using hexane/ethyl acetate (8:2) as eluent to afford 34 as an orange solid (0.7 g). LRMS [calculated for $(M+1)^+$:510] observed: 510.

EXAMPLE 29

4-BROMO-N-(1-PHENETHYL-PIPERIDIN-3-YLMETHYL)-N-PHENYL-BENZENESULFONAMIDE

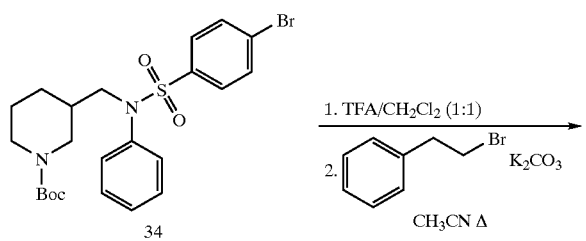

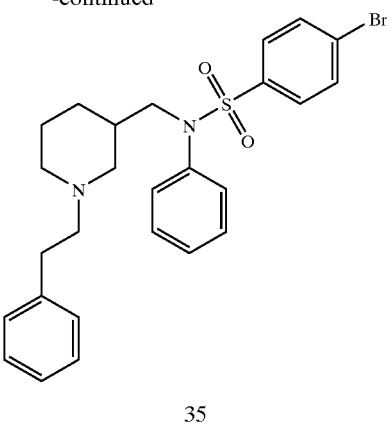

To a vial were added 34 (0.15 g, 0.29 mmol) and a 1:1 solution of trifluoroacetic acid/dichloromethane (1 mL). The reaction mixture was stirred at room temperature for 30 minutes. Then the mixture was evaporated and dried under vacuum. Then, acetonitrile (0.55 mL), potassium carbonate (0.122 mg, 0.88 mmol) and (2-bromoethyl)benzene were added. The reaction mixture was stirred at 50° C. overnight. Then the mixture was poured into a separatory funnel and ethyl acetate (10 mL) was used for the extraction. The organic layer was sequentially washed with a 10% NaOH solution and with brine, dried over $Na_2SO_4$, filtered and evaporated. Finally the crude product was purified by preparative TLC using dicloromethane/methanol (95:5) as eluent to afford 35 as a colorless oil (0.97 g). LRMS [calculated for $(M+1)^+$:514] observed: 514.

EXAMPLE 30

N-(1-phenylisopropyl-piperidin-3-ylmethyl)-N-phenyl-methanesulfonamide

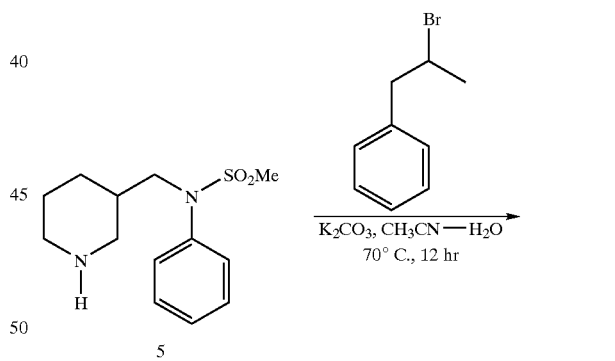

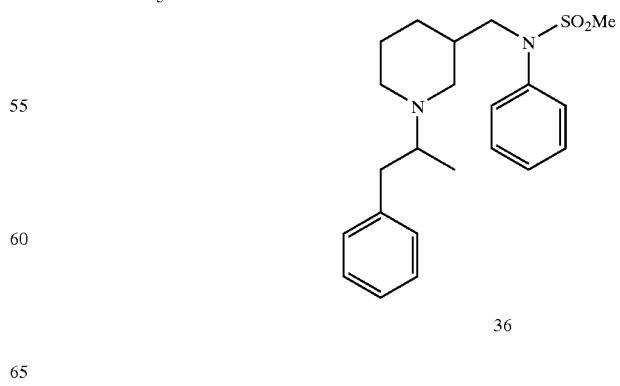

The mixture of amine 5 (30 mg, 0.11 mmol), (2-bromopropyl)-benzene (0.052 mL), $CH_3CN$ (4 mL), $H_2O$ (4 mL), K$_2$CO$_3$ (0.047 g, 0.34 mmol) was stirred at 70° C. for 12 hrs. After cool down to room temperature, the organic layer was separated. Aqueous layer was extracted with EtOAc (2×10 mL). The combined organic solution was dried with Na$_2$SO$_4$, filtered and evaporated. The crude product was purified by flash silica gel chromatography (20% EtOAc in hexane) to give 36 as a colorless oil (18 mg, 42%). $^1$H-NMR (300 MHz, CDCl$_3$) δ 7.40–7.10 (m, 10H), 3.62 (d, 2H), 2.95–2.75 (m, 7H), 2.40 (m, 2H), 2.10 (m, 1H), 1.80–1.60 (m, 5H), 1.50 (m, 1H), 1.10 (m, 1H) 0.90 (d, 3H) ppm; LRMS [calculated for C$_{22}$H$_{31}$N$_2$O$_2$S, (M+1)$^+$] 387, found 387.

EXAMPLE 31

3-[(2-thiophenesulfonyl-phenyl-amino)-methyl]-piperidine-1-carboxylic acid tert-butyl ester

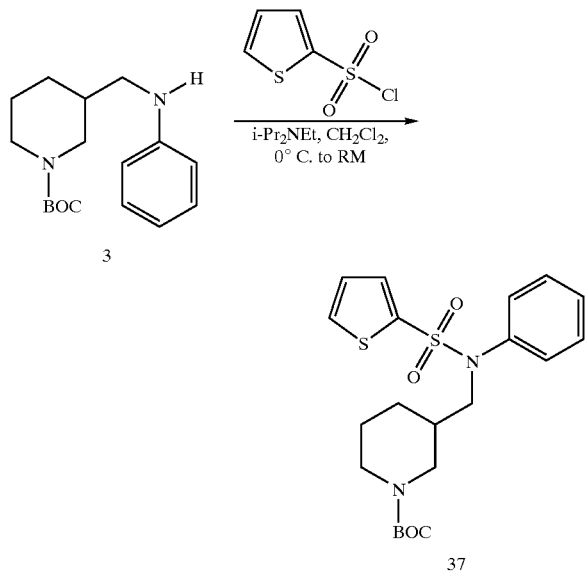

To a solution of 3-phenylaminomethyl-piperidine-1-carboxylic acid tert-butyl ester 3 (192 mg, 0.66 mmol), i-Pr$_2$NEt (0.2 mL, 1.18 mmol) in CH$_2$Cl$_2$ (5 mL) at 0° C. was added 2-thiophenesulfonyl chloride (120 mg, 0.66 mmol). The mixture was warmed up to room temperature and stirred for 3 hrs. Aqueous NaHCO$_3$ (5 mL) was added. The two layers were separated. Aqueous layer was extracted with CH$_2$Cl$_2$ (2×5 mL). The combined organic solution was dried with Na$_2$SO$_4$, filtered and evaporated. The crude product was purified by silica gel chromatography (20% EtOAc in hexane) to afford 37 as a white solid (245 mg, 85%). $^1$H-NMR (300 MHz, CDCl$_3$) δ 7.60 (d, 1H), 7.40–7.26 (m, 4H), 7.16–7.07 (m, 3H), 3.98 (m, 1H), 3.46 (m, 1H), 3.48 (m, 2H), 2.84 (m, 1H), 2.68 (dd, 1H), 1.83–1.20 (m, 5H), 1.48 (s, 9H) ppm; $^{13}$C-NMR (75 MHz, CDCl$_3$) δ 154.95, 139.12, 138.47, 132.83, 132.19, 129.46, 128.81, 128.58, 127.59, 79.73, 53.90, 47.74, 44.55, 34.68, 29.96, 28.72, 28.30, 24.35 ppm.

EXAMPLE 32

N-phenyl-N-piperidin-3-ylmethyl-2-thiophenesulfonamide

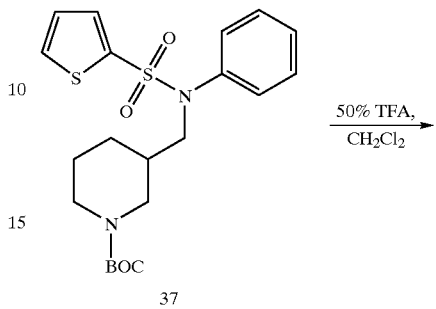

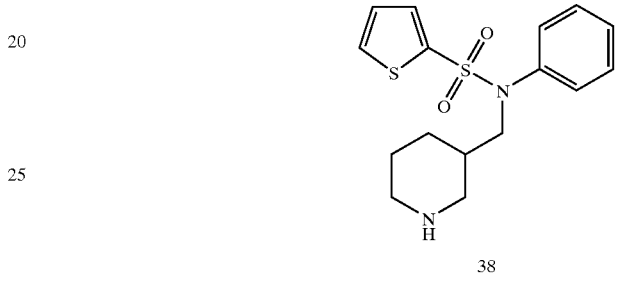

To a solution of N-(1-Boc-piperidin-3-ylmethyl)-N-phenyl-2-thiophene sulfonamide 37 (45 mg, 0.103 mmol) in CH$_2$Cl$_2$ (2 mL) at 0° C. was added TFA (2 mL). After stirring for 1 hr, solvent and excess TFA was removed by evaporation. The residue was dissolved in 5 mL of 5% HCl, washed with EtOAc (2×5 mL). The organic solution was discarded. The aqueous solution was neutralized with K$_2$CO$_3$, extracted with EtOAc (2×5 mL). The combined extracts were dried with Na$_2$SO$_4$, filtered and evaporated to afford 38 as a white solid. $^1$H-NMR (300 MHz, CDCl$_3$) δ 7.65 (d, 1H), 57.38–7.32 (m, 4H), 7.05–7.29 (m, 3H), 3.65 (m, 2H), 3.52 (m, 2H), 2.90 (m, 2H), 1.99–1.29 (m, 6H) ppm; $^{13}$C-NMR (75 MHz, CDCl$_3$) δ 138.63, 137.61, 133.40, 132.84, 129.82, 129.18, 128.62, 127.85, 54.01, 47.74, 45.16, 32.96, 29.96, 26.36 ppm.

EXAMPLE 33

N-(1-phenethyl-piperidin-3-ylmethyl)-N-phenyl-thiophenesulfonamide

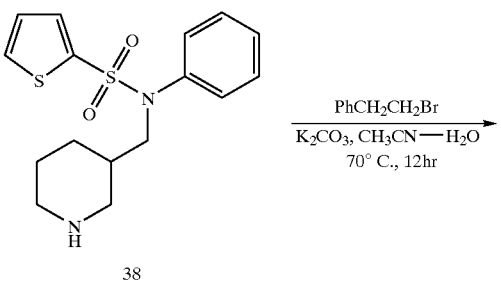

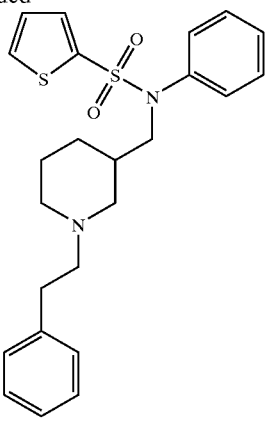

39

The mixture of amine 38 (29 mg, 0.086 mmol), (2-bromoethyl)-benzene (0.017 mL 0.13 mmol), CH₃CN (2 mL), H₂O (2 nL), K₂CO₃ (35 mg, 0.25 mmol) was stirred at 70° C. for 12 hrs. After cool down to room temperature, the organic layer was separated. Aqueous layer was extracted with EtOAc (2×5 mL). The combined organic solution was dried with Na₂SO₄, filtered and evaporated. The crude product was purified by flash silica gel chromatography (20% EtOAc in hexane) to give 39 as a colorless oil (18.9 mg, 50%). LRMS [calculated for $C_{24}H_{29}N_2O_2S_2$, $(M+1)^+$] 441, found 441.

EXAMPLE 34

3-[(8-Ouinolinesulfonyl-phenyl-amino)-methyl]-piperidine-1-carboxylic acid tert-butyl ester

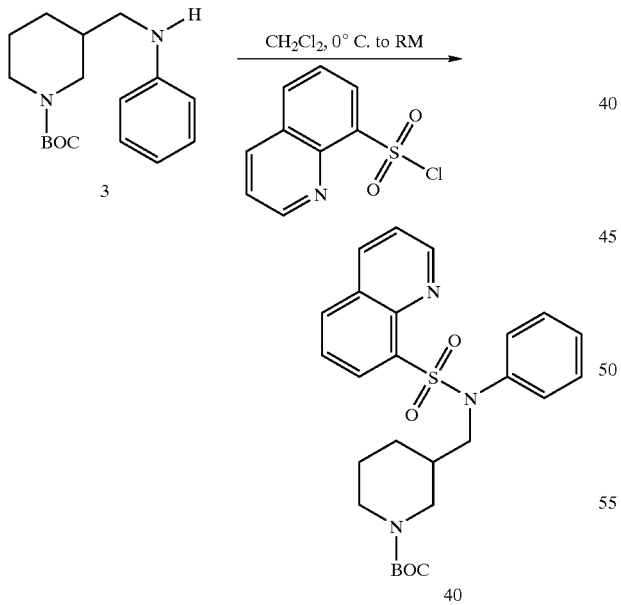

To a solution of 3-phenylaminomethyl-piperidine-1-carboxylic acid tert-butyl ester 3 (150 mg, 0.52 mmol), in CH₂Cl₂ (5 mL) at 0° C. was added 8-Quinolinesulfonyl chloride (118 mg, 0.52 mmol). The mixture was warmed up to room temperature and stirred for 3 hrs. Aqueous NaHCO₃ (5 mL) was added. The two layers were separated. Aqueous layer was extracted with CH₂Cl₂ (2×5 mL). The combined organic solution was dried with Na₂SO₄, filtered and evaporated. The crude product was purified by silica gel chromatography (20% EtOAc in hexane, then 100% CH₂Cl₂) to afford 40 as a white solid (172.4 mg, 68%). ¹H-NMR (300 MHz, CDCl₃) δ 9.08 (d, 1H), 8.31 (d, 1H), 8.20 (d, 1H), 7.98 (d, 1H), 7.61 (t, 1H), 7.24 (t, 1H), 7.17 (m, 3H), 7.06 (m, 2H), 4.30–4.02 (m, 4H), 2.80–2.62 (m, 2H), 1.83–1.20 (m; SH), 1.52 (s, 9H) ppm; ¹³C-NMR (75 MHz, CDCl₃) δ 155.03, 151.36, 144.41, 139.57, 137.08, 136.82, 134.05, 133.63, 129.20, 128.95, 127.87, 125.64, 122.27, 79.58, 56.92, 48.57, 44.93, 35.64, 28.77, 24.84 ppm.

EXAMPLE 35

N-phenyl-N-piperidin-3-ylmethyl-8-Quinolinesulfonamide

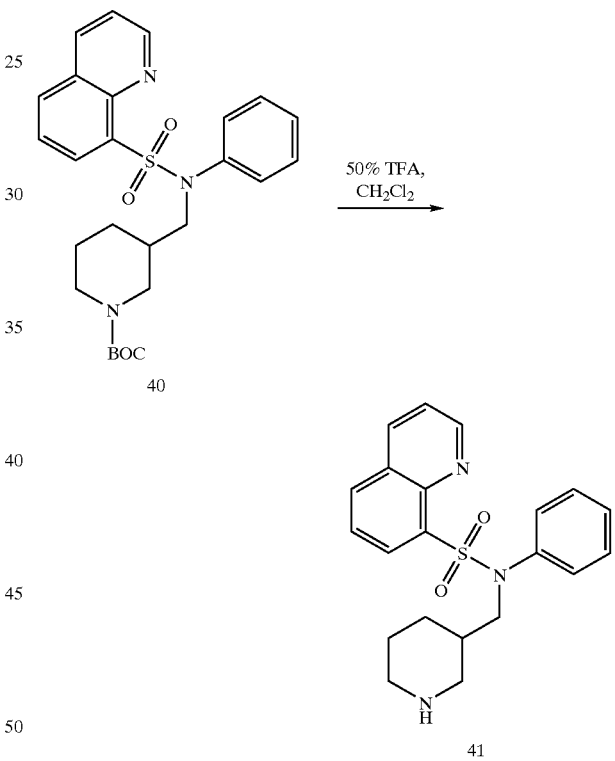

To a solution of N-(1-Boc-piperidin-3-ylmethyl)-N-phenyl-8-Quinoline sulfonamide 40 (150 mg, 0.31 mmol) in CH₂Cl₂ (2 mL) at 0° C. was added TFA (2 mL). After stirring for 1 hr, solvent and excess TFA was removed by evaporation. The residue was dissolved in 5 mL of 5% HCl, washed with EtOAc (2×S mL). The organic solution was discarded. The aqueous solution was neutralized with K₂CO₃, extracted with EtOAc (2×5 mL). The combined extracts were dried with Na₂SO₄, filtered and evaporated to afford 41 as a white solid. LRMS [calculated for $C_{21}H_{24}N_3O_2S$, $(M+1)^+$] 382, found 382.

EXAMPLE 36

N-(1-phenethyl-piperidin-3-ylmethyl)-N-phenyl-8-Quinoline sulfonamide

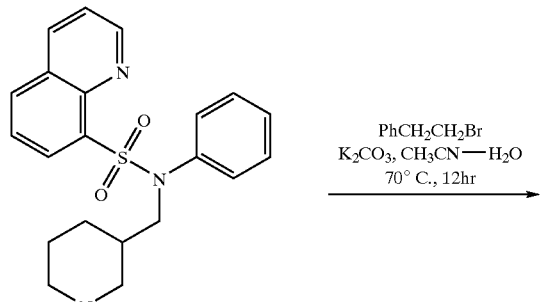

41

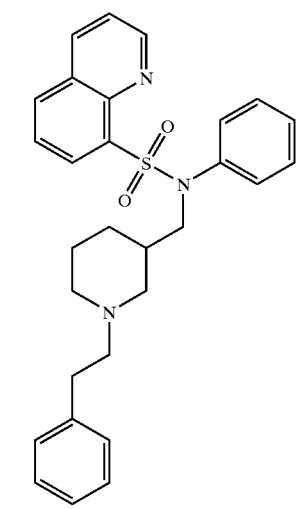

42

The mixture of amine 41 (91 mg, 0.238 mmol), (2-bromoethyl)-benzene (0.034 mL 0.26 mmol), CH$_3$CN (2 mL), H$_2$O (2 mL), K$_2$CO$_3$ (70 mg, 0.50 mmol) was stirred at 70° C. for 12 hrs. After cool down to room temperature, the organic layer was separated. Aqueous layer was extracted with EtOAc (2×5 mL). The combined organic solution was dried with Na$_2$SO$_4$, filtered and evaporated. The crude product was purified by flash silica gel chromatography (20% EtOAc in hexane) to give 42 as a colorless solid (85 mg, 74%). LRMS [calculated for C$_{29}$H$_{32}$N$_3$O$_2$S, (M+1)$^+$] 486, found 486.

EXAMPLE 37

Effects of 16 in an Animal Model of Psychosis

The non-competitive NMDA receptor antagonist MK-801 induces stereotypies and hyperactivity in rodents (see: Carlsson, M. and Carlsson, A., J. Neural Transm., 75, 221 (1989)) by interacting with the NMDA receptor-associated ion channel. Phencyclidine, which also interferes with the NMDA receptor, produces psychotic effects in humans similar in many respects to schizophrenia. These findings suggest that a deficiency in glutamate transmission may be responsible in the pathology of schizophrenia (Korhuber, J. and Kornhuber, M. E., Life Sci., 39, 669 (1986)). The neuroleptics haloperidol, clozapine and raclopride are able to reverse the behavioral changes induced by MK-801 in rats (Gattaz, W. F., Schummer, B. and Behrens, S., J. Neural Transm., 96, 227 (1994)). Therefore the MK-801-induced activity and stereotypies in rats may represent an appropriate animal model to test the potential efficacy of antipsychotic drugs.

Male Wistar rats (Iffa Credo, St Germain/l'Arbresle, France), weight 250–300 g were housed 2 per cage on a 12 h/12 h light dark cycle (lights on at 7.00 a.m.) at a room temperature of 21±2° C. for a minimum of 5 days before testing. All animals had access to commercial food and tap water ad libitum. Test compound was formulated in 50 mM sodium acetate.

On the day of the experiment, rats were treated with either reference drug vehicle, the reference drugs haloperidol or clozapine the test compound vehicle or test compounds. After administration, the rats were returned to their home cages for 15 minutes. The haloperidol, clozapine, test compound and vehicle treated animals received then an i.p. injection of 0.3 mg/kg MK-801. The remaining rats treated with placebo received a second injection of vehicle. The standard injection volume was 2.0 mL/kg. After 10 minutes in the home cages, rats were transferred to the test box (Plexiglas, 29×12×12 cm), 5 minutes before the assessment for accomodation. The test box was cleaned with 70% ethanol before each assessment. Stereotypies, defined as wall-contacts with the snout, and locomotion, defined as turn-rounds of 180°, were assessed during 5 minute periods.

Compound 16 caused a dose-dependent reduction of MK-801-induced locomotion and stereotypies when dosed at 1.0, 2.5 and 5.0 mg/kg i.p.

EXAMPLE 38

EFFECTS OF 6 IN THE LEARNED HELPLESSNESS TEST IN RATS

The objective of this study was to evaluate the potential antidepressant activity of compounds in the learned helplessness test in rats.

Male rats (Wistar, Iffa Credo, St.-Germain/1"Arbresle, France) with initial weight of 180–200 g at the beginning of the experiments were housed 3 per cage under dark cycle of 12 h–12 h (light on at 7:00 a.m., off at 7:00 p.m.) at a room temperature of 21±1° C., with a minimum 50% humidity, for a minimum of 7 days before the experiments. They had free access to commercial rat chow (UFAC, Vigney, France, ref 811002) and tap water. The learned helplessness test included two phases over 5 days.

Phase 1: Helplessness induction

On day 1, inescapable electric foot-shocks were delivered individually to rats in a Plexiglas chamber (20 cm×16 cm×16 cm [l×w×h]) with a floor consisting of stainless-steel rods. A constant-current shocker (LETICA LI 100-26, Barcelona, Spain) was used to deliver inescapable shocks (0.8 m A scrambled DC current; 10 s duration every 20 s) over 60 minutes. "Non-helplessness" control rats were placed for 1 h in identical chambers without shocking.

Phase 2: Conditional Avoidance Training

Avoidance training in automated two-way shuttle-box (LETICA LI916, Barcelona, Spain) took place on day 3, 4, and 5. The shuttle-box is divided into two equal-sized chambers connected by a 10×10 cm opening. Animals were placed singly into the shuttle-box, allowed to habituate to the test environment for 5 minutes (first session only) and then subjected to 30 avoidance trials with between-trial intervals of 30 s. During the first 3 s of each trial, a light signal was presented, allowing the animals to avoid shocks by moving to the other side of box. If the animal did not respond within this period, the light remained on and a 0.55 mA shock of 3 s duration was applied. If no response occurred during the shock period, the shock and the light were terminated after 3 s and this was defined as an escape failure.

"Non-helplessness" controls, which received no shocks, were given vehicle (2 mg/kg NaCl 0.9% i.p.). Animals with inescapable shocks were administrated with 2 mL/kg vehicle NaCl 0.9% i.p. ("helpless control" group). Compound 6 (2, 5, 19 mg/kg i.p.) and vehicle (sodium acetate 50 mM, pH 3.0). Imipramine HCl (Sigma Chemicals, St-Louis, USA, 16 mg/kg i.p.) was used as reference compound.

Drug or vehicles were given over 5 consecutive days, 6 h after shock pretreatment on day 1, then twice daily except on day 5 when they were treated singly. The animals were tested 30 minutes after the first injection on day 3, 4, and 5.

Individual comparison showed that there was a significant difference between the "helpless" and "non-helpless" control groups; "helpless" controls made considerably more escape failures than "non-helpless" controls and continued to do so throughout the avoidance test.

Compound 6 is active in the learned helplessness test at a dose of 5 mg/kg. The results indicate that 6 may have antidepressant effects in humans.

EXAMPLE 39
Radioligand Binding Assays

The NMDA receptor (PCP site) screen was conducted according to Goldman, M. E. et al. FEBS *Letters* 85, 190, 333. The norepinephrine transporter screen was conducted according to Galli A et al. *J. Exp. Biol.* 1995, 198, 2197. The dopamine and serotonin transporter screens were conducted according to Gu, H. et al. *J. Biol. Chem.* 1994, 269(10), 7124. The sigma-1 screen was conducted according to de Costa B. R. *FEBS* 1989, 251, 53.

| Compound | GPCR | $IC_{50}$ (nM) |
|---|---|---|
| 5 | NMDA (PCP site) | 108 |
| 21 | NE Transporter | 62 |
| 21 | Dopamine Transporter | −2840 |
| 21 | 5-HT Transporter | 2800 |
| 6 | Sigma-1 (human) | 118 |
| 12 | Sigma-1 (human) | 550 |
| 16 | Sigma-1 (human) | 22 |

EXAMPLE 40
In vivo Analgesia Experiments

The acetic acid writhing model was conducted according to Inoue K. et al. *Arzneim. Forsch* 1991, 41(I), 235. The formalin model was conducted according to Hunskaar, S. et al. *J. Neurosci Meth.* 1985, 14, 69. The tail flick model was conducted according to D'Amour F. E. and Smith D. L. *J. Pharmacol. Exp. Ther.* 1941, 72, 74. Compound 6 was administered intravenously.

| | $ED_{50}$ (mg/kg) | | |
|---|---|---|---|
| Compound | Acetic acid Writhing | Formalin | Tail Flick |
| 6 | 7.8 | 18 | 23 |

Incorporation by Reference

All of the publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by B:

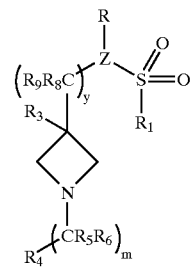

wherein
Z represents N or CR;
m is 0, 1, 2, 3 or 4;
p is 1, 2, or 3;
y is 0, 1 or 2;
R represents H, alkyl, cycloalkyl, aryl, heteroaryl, aralkyl, or heteroaralkyl;
$R_1$ represents $NR_2$, alkyl, cycloalkyl, aryl, heteroaryl, aralkyl, or heteroaralkyl;
R and $R_1$ may be connected through a covalent bond;
$R_2$ represents independently for each occurrence H, alkyl, fluoroalkyl, aryl, heteroaryl, or cycloalkyl;
$R_3$ represents independently for each occurrence H, alkyl, aryl, $OR_2$, $OC(O)R_2$, $CH_2OR_2$, or $CO_2R_2$;
$R_4$ represents H, alkyl, aryl, heteroaryl, alkenyl, or cycloalkyl;
$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is C(O);
$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_9R_9$ taken together is C(O);
Y represents independently for each occurrence $OR_2$, $N(R_2)_2$, $SR_2$, $S(O)R_2$, $S(O)_2R_2$, or $P(O)(OR_2)_2$;
any two instances of $R_2$ may be connected through a covalent bond;
a covalent bond may connect $R_4$ and an instance of $R_5$ or $R_6$;
any two instances of $R_5$ and $R_6$ may be connected through a covalent bond;
any two geminal or vicinal instances of $R_8$ and $R_9$ may be connected through a covalent bond; and
the stereochemical configuration at any stereocenter of a compound represented by B is R, S, or a mixture of these configurations.

2. The compound of claim 1, wherein m is 2.
3. The compound of claim 1, wherein y is 1.
4. The compound of claim 1, wherein R represents aryl or heteroaryl.
5. The compound of claim 1, wherein $R_1$ represents alkyl or aryl.

6. The compound of claim 1, wherein $R_3$ represents independently for each occurrence H or alkyl.

7. The compound of claim 1, wherein $R_4$ represents cycloalkyl, aryl, or heteroaryl.

8. The compound of claim 1, wherein $R_5$ and $R_6$ are selected independently for each occurrence from the group consisting of H, alkyl, $OR_2$, aryl, heteroaryl, and F.

9. The compound of claim 1, wherein $R_8$ and $R_9$ are selected independently for each occurrence from the group consisting of H, alkyl, $OR_2$, aryl, heteroaryl, and F.

10. The compound of claim 1, wherein m is 2; and y is 1.

11. The compound of claim 1, wherein m is 2; y is 1; and R represents aryl or heteroaryl.

12. The compound of claim 1, wherein m is 2; y is 1; R represents aryl or heteroaryl; and $R_1$ represents alkyl or aryl.

13. The compound of claim 1, wherein m is 2; y is 1; R represents aryl or heteroaryl; $R_1$ represents alkyl or aryl; and $R_3$ represents independently for each occurrence H or alkyl.

14. The compound of claim 1, wherein m is 2; y is 1; R represents aryl or heteroaryl; $R_1$ represents alkyl or aryl; $R_3$ represents independently for each occurrence H or alkyl; and $R_4$ represents cycloalkyl, aryl, or heteroaryl.

15. The compound of claim 1, wherein m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; and $R_5$ and $R_6$ are selected independently for each occurrence from the group consisting of H, alkyl, $OR_2$, aryl, heteroaryl, and F.

16. The compound of claim 1, wherein m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

17. A compound represented by C:

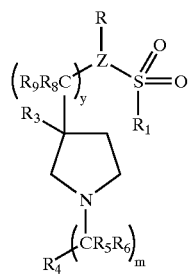

wherein

Z represents N or CR;

m is 0, 1, 2, 3 or 4;

p is 1, 2, or 3;

y is 0, 1 or 2;

R represents H, alkyl, cycloalkyl, aryl, heteroaryl, aralkyl, or heteroaralkyl;

$R_1$ represents $NR_2$, alkyl, cycloalkyl, aryl, heteroaryl, aralkyl, or heteroaralkyl;

R and $R_1$ may be connected through a covalent bond;

$R_2$ represents independently for each occurrence H, alkyl, fluoroalkyl, aryl, heteroaryl, or cycloalkyl;

$R_3$ represents independently for each occurrence H, alkyl, aryl, $OR_2$, $OC(O)R_2$, $CH_2OR_2$, or $CO_2R_2$;

$R_4$ represents H, alkyl, aryl, heteroaryl, alkenyl, or cycloalkyl;

$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is C(O);

$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8SR_9$ taken together is C(O);

Y represents independently for each occurrence $OR_2$, $N(R_2)_2$, $SR_2$, $S(O)R_2$, $S(O)_2R_2$, or $P(O)(OR_2)_2$;

any two instances of $R_2$ may be connected through a covalent bond;

a covalent bond may connect $R_4$ and an instance of $R_5$ or $R_6$;

any two instances of $R_5$ and $R_6$ may be connected through a covalent bond;

any two geminal or vicinal instances of $R_5$ and $R_6$ may be connected through a covalent bond; and the stereochemical configuration at any stereocenter of a compound represented by C is R or S, or a mixture of these configurations.

18. The compound of claim 17, wherein m is 2.

19. The compound of claim 17, wherein y is 1.

20. The compound of claim 17, wherein R represents aryl or heteroaryl.

21. The compound of claim 17, wherein $R_1$ represents alkyl or aryl.

22. The compound of claim 17, wherein $R_3$ represents independently for each occurrence H or alkyl.

23. The compound of claim 17, wherein $R_4$ represents cycloalkyl, aryl, or heteroaryl.

24. The compound of claim 17, wherein $R_5$ and $R_6$ are selected independently for each occurrence from the group consisting of H, alkyl, $OR_2$, aryl, heteroaryl, and F.

25. The compound of claim 17, wherein $R_8$ and $R_9$ are selected independently for each occurrence from the group consisting of H, alkyl, $OR_2$, aryl, heteroaryl, and F.

26. The compound of claim 17, wherein m is 2; and y is 1.

27. The compound of claim 17, wherein m is 2; y is 1; and R represents aryl or heteroaryl.

28. The compound of claim 17, wherein m is 2; y is 1; R represents aryl or heteroaryl; and $R_1$ represents alkyl or aryl.

29. The compound of claim 17, wherein m is 2; y is 1; R represents aryl or heteroaryl; $R_1$ represents alkyl or aryl; and $R_3$ represents independently for each occurrence H or alkyl.

30. The compound of claim 17, wherein m is 2; y is 1; R represents aryl or heteroaryl; $R_1$ represents alkyl or aryl; $R_3$ represents independently for each occurrence H or alkyl; and $R_4$ represents cycloalkyl, aryl, or heteroaryl.

31. The compound of claim 17, wherein m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; and $R_5$ and $R_6$ are selected independently for each occurrence from the group consisting of H, alkyl, $OR_2$, aryl, heteroaryl, and F.

32. The compound of claim 17, wherein m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

33. A compound represented by D:

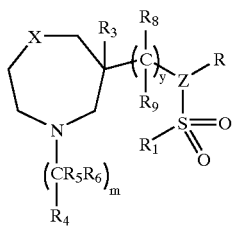

wherein
X represents $C(R_3)_2$, O, S, SO, $SO_2$, $NR_2$, $NC(O)R_1$, $NC(O)OR_2$, $NS(O)_2R_1$, or C=O;
Z represents N or CR;
m is 0, 1, 2, 3 or 4;
p is 1, 2, or 3;
y is 0, 1, or 2;
R represents H, alkyl, cycloalkyl, aryl, heteroaryl, aralkyl, or heteroaralkyl;
$R_1$ represents $NR_2$, alkyl, cycloalkyl, aryl, heteroaryl, aralkyl, or heteroaralkyl;
R and $R_1$ may be connected through a covalent bond;
$R_2$ represents independently for each occurrence H, alkyl, fluoroalkyl, aryl, heteroaryl, or cycloalkyl;
$R_3$ represents independently for each occurrence H, alkyl, aryl, $OR_2$, $OC(O)R_2$, $CH_2OR_2$, or $CO_2R_2$;
$R_4$ represents independently for each occurrence H, alkyl, aryl, heteroaryl, alkenyl, or cycloalkyl;
$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is C(O);
$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8R_9$ taken together is C(O);
Y represents independently for each occurrence $OR_2$, $N(R_2)_2$, $SR_2$, $S(O)R_2$, $S(O)_2R_2$, or $P(O)(OR_2)_2$;
any two instances of $R_2$ may be connected through a covalent bond;
a covalent bond may connect $R_4$ and an instance of $R_5$ or $R_6$;
any two instances of $R_5$ and $R_6$ may be connected through a covalent bond;
any two geminal or vicinal instances of $R_8$ and $R_9$ may be connected through a covalent bond; and
the stereochemical configuration at any stereocenter of a compound represented by D is R, S, or a mixture of these configurations.

34. The compound of claim 33, wherein X is O or $NR_2$.
35. The compound of claim 33, wherein m is 2.
36. The compound of claim 33, wherein y is 1.
37. The compound of claim 33, wherein R represents aryl or heteroaryl.
38. The compound of claim 33, wherein $R_1$ represents alkyl or aryl.
39. The compound of claim 33, wherein $R_3$ represents independently for each occurrence H or alkyl.
40. The compound of claim 33, wherein $R_4$ represents cycloalkyl, aryl, or heteroaryl.
41. The compound of claim 33, wherein $R_5$ and $R_6$ are selected independently for each occurrence from the group consisting of H, alkyl, $OR_2$, aryl, heteroaryl, and F.
42. The compound of claim 33, wherein $R_8$ and $R_9$ are selected independently for each occurrence from the group consisting of H, alkyl, $OR_2$, aryl, heteroaryl, and F.
43. The compound of claim 33, wherein X is O or $NR_2$; and m is 2.
44. The compound of claim 33, wherein X is O or $NR_2$; and y is 1.
45. The compound of claim 33, wherein X is O or $NR_2$; m is 2; and y is 1.
46. The compound of claim 33, wherein X is O or $NR_2$; m is 2; y is 1; and R represents aryl or heteroaryl.
47. The compound of claim 33, wherein X is O or $NR_2$; m is 2; y is 1; R represents aryl or heteroaryl; and $R_1$ represents alkyl or aryl.
48. The compound of claim 33, wherein X is O or $NR_2$; m is 2; y is 1; R represents aryl or heteroaryl; $R_1$ represents alkyl or aryl; and $R_3$ represents independently for each occurrence H or alkyl.
49. The compound of claim 33, wherein X is O or $NR_2$; m is 2; y is 1; R represents aryl or heteroaryl; $R_1$ represents alkyl or aryl; $R_3$ represents independently for each occurrence H or alkyl; and $R_4$ represents cycloalkyl, aryl, or heteroaryl.
50. The compound of claim 33, wherein X is O or $NR_2$; m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; and $R_5$ and $R_6$ are selected independently for each occurrence from the group consisting of H, alkyl, $OR_2$, aryl, heteroaryl, and F.
51. The compound of claim 33, wherein X is O or $NR_2$; m is 2; y is 1; R represents aryl or heteroaryl; $R_1$ represents alkyl or aryl; $R_3$ represents independently for each occurrence H or alkyl; $R_4$ represents cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.
52. The compound of claim 1, 17, or 33, wherein said compound is a single stereoisomer.
53. The compound of claim 1, 17, or 33, wherein said compound has an $IC_{50}$ less than 1 $\mu$M in an assay based on a mammalian GPCR or ligand-gated ion channel.
54. The compound of claim 1, 17, or 33, wherein said compound has an $IC_{50}$ less than 100 nM in an assay based on a mammalian GPCR or ligand-gated ion channel.
55. The compound of claim 1, 17, or 33, wherein said compound has an $IC_{50}$ less than 10 nM in an assay based on a mammalian GPCR or ligand-gated ion channel.
56. The compound of claim 1, 17, or 33, wherein said compound has an $IC_{50}$ less than 1 $\mu$M in an assay based on a mammalian GPCR.
57. The compound of claim 19, wherein said mammalian GPCR is an NMDA receptor, a norepinephrine transporter or a sigma receptor.
58. The compound of claim 6, wherein said compound has an $IC_{50}$ less than 100 nM in an assay based on a mammalian GPCR.
59. The compound of claim 58, wherein said mammalian GPCR is an NMDA receptor, a norepinephrine transporter or a sigma receptor.
60. The compound of claim 1, 17, or 33, wherein said compound has an $IC_{50}$ less than 10 nM in an assay based on a mammalian GPCR.
61. The compound of claim 60, wherein said mammalian GPCR is an NMDA receptor, a norepinephrine transporter or a sigma receptor.

62. A formulation, comprising a compound of claim 17, or 33; and a pharmaceutically acceptable excipient.

63. A method of treating an acute or chronic ailment, disease or malady in a mammal that is due to an abnormality in a biochemical or physiological process associated with a G-protein-coupled receptor or ligand-gated ion channel, comprising the step of administering to said mammal a therapeutically effective amount of a compound of claim 1, 17, or 33.

64. The method of claim 63, wherein said mammal is a primate, equine, canine or feline.

65. The method of claim 63, wherein said mammal is a human.

66. The method of claim 63, wherein said compound is administered orally.

67. The method of claim 63, wherein said compound is administered intravenously.

68. The method of claim 63, wherein said compound is administered sublingually.

69. The method of claim 63, wherein said compound is administered ocularly.

70. The method of claim 63, wherein said compound is administered transdermally.

71. The method of claim 63, wherein said compound is administered rectally.

72. The method of claim 63, wherein said compound is administered vaginally.

73. The method of claim 63, wherein said compound is administered nasally.

74. A method of treating a psychiatric disorder in a mammal, comprising the step of:

administering to said mammal a therapeutically effective amount of a compound of claim 1, 17, or 33.

75. The method of claim 74, wherein said psychiatric disorder is a psychosis.

76. The method of claim 74, wherein said psychiatric disorder is schizophrenia.

77. The method of claim 74, wherein said psychiatric disorder is paranoia, manic depression, or depression.

78. The method of claim 74, wherein said mammal is a primate, equine, canine or feline.

79. The method of claim 74, wherein said mammal is a human.

80. The method of claim 74, wherein said compound is administered orally.

81. The method of claim 74, wherein said compound is administered intravenously.

82. The method of claim 74, wherein said compound is administered sublingually.

83. The method of claim 74, wherein said compound is administered ocularly.

84. The method of claim 74, wherein said compound is administered transdermally.

85. The method of claim 74, wherein said compound is administered rectally.

86. The method of claim 74, wherein said compound is administered vaginally.

87. The method of claim 74, wherein said compound is administered nasally.

88. A method of treating a mammal suffering from an anxiety disorder, a dissociative disorder, a mood disorder, a personality disorder, a psychosexual disorder, an eating disorder, drug addiction, drug dependence, depression, manic depression, paranoia, psychosis, schizophrenia, or inflammatory pain, comprising the step of:

administering to said mammal a therapeutically effective amount of a compound of claim 1, 17, or 33.

89. The method of claim 88, wherein said mammal is a primate, equine, canine or feline.

90. The method of claim 88, wherein said mammal is a human.

91. The method of claim 88, wherein said compound is administered orally.

92. The method of claim 88, wherein said compound is administered intravenously.

93. The method of claim 88, wherein said compound is administered sublingually.

94. The method of claim 88, wherein said compound is administered ocularly.

95. The method of claim 88, wherein said compound is administered transdermally.

96. The method of claim 88, wherein said compound is administered rectally.

97. The method of claim 88, wherein said compound is administered vaginally.

98. The method of claim 88, wherein said compound is administered nasally.

* * * * *